United States Patent
Zahler et al.

(10) Patent No.: US 9,221,787 B2
(45) Date of Patent: Dec. 29, 2015

(54) SULPHONAMINE COMPOUNDS AND METHODS OF MAKING AND USING SAME

(75) Inventors: Robert Zahler, Pennington, NJ (US); Hazel Joan Dyke, Harlow (GB); Thomas David Pallin, Harlow (GB); Susan Mary Cramp, Harlow (GB)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 13/878,958

(22) PCT Filed: Oct. 12, 2011

(86) PCT No.: PCT/US2011/055987
§ 371 (c)(1),
(2), (4) Date: Apr. 11, 2013

(87) PCT Pub. No.: WO2012/051318
PCT Pub. Date: Apr. 19, 2012

(65) Prior Publication Data
US 2013/0217759 A1    Aug. 22, 2013

Related U.S. Application Data

(60) Provisional application No. 61/392,108, filed on Oct. 12, 2010, provisional application No. 61/420,050, filed on Dec. 6, 2010.

(51) Int. Cl.
| | | |
|---|---|---|
| *C07D 333/38* | (2006.01) | |
| *C07D 333/68* | (2006.01) | |
| *C07D 409/04* | (2006.01) | |
| *C07D 495/04* | (2006.01) | |

(52) U.S. Cl.
CPC ............ *C07D 333/68* (2013.01); *C07D 333/38* (2013.01); *C07D 409/04* (2013.01); *C07D 495/04* (2013.01)

(58) Field of Classification Search
CPC .. C07D 333/38; C07D 333/68; C07D 409/04; C07D 495/04
See application file for complete search history.

(56) References Cited

U.S. PATENT DOCUMENTS

| | | | |
|---|---|---|---|
| 8,119,663 B2 | 2/2012 | Heimbach et al. | |
| 2002/0142028 A1* | 10/2002 | Elliesen et al. | 424/449 |
| 2004/0167128 A1 | 8/2004 | Comess et al. | |
| 2008/0312231 A1 | 12/2008 | Merla et al. | |
| 2013/0053364 A1 | 2/2013 | Dyke et al. | |
| 2013/0123235 A1 | 5/2013 | Clark et al. | |
| 2013/0331420 A1 | 12/2013 | Dyke et al. | |
| 2014/0073623 A1 | 3/2014 | Cramp et al. | |
| 2014/0080822 A1 | 3/2014 | Cramp et al. | |
| 2014/0088078 A1 | 3/2014 | Cramp et al. | |

FOREIGN PATENT DOCUMENTS

| | | |
|---|---|---|
| WO | WO 2008131947 | 11/2008 |
| WO | WO 2009017719 A2 * | 2/2009 |
| WO | WO-2010/065879 A2 | 6/2010 |

OTHER PUBLICATIONS

Chemical Abstract Services, STN, 2001, RN 331750-29-9.*
Chan, L., et al. (2004) "Discovery of Thiophene-2-carboxylic Acids as Potent Inhibitors of HCV NS5B Polymerase and HCV Subgenomic RNA Replication. Part 1: Sulfonamides," *Bioorganic & Medicinal Chemistry Letters*. vol. 14, pp. 793-796.
Database Registry [Online] (Aug. 24, 2008), *Chemical Abstracts Service*, XP002664461.
Database Registry [Online] (Jan. 20, 2009), Chemical Abstracts Service, XP002664460.
Database Registry [Online] (Jan. 23, 2009), Chemical Abstracts Service, XP002664459.
Database Registry [Online] (Jan. 27, 2009), Chemical Abstracts Service, XP002664458.
Database Registry [Online] (Sep. 15, 2009), Chemical Abstracts Service, XP002664454.
Database Registry [Online], (Sep. 11, 2009) Chemical Abstracts Service, XP002664455.
Database Registry [Online], (Oct. 4, 2010) Chemical Abstracts Service, XP002664453.
Database Registry [Online} (Jun. 7, 2009), Chemical Abstracts Service, XP002664456.
Database Registry [Online] (Mar. 13, 2007), Chemical Abstracts Service, XP002664463.
Database Registry [Online] (Jan. 28, 2009), Chemical Abstracts Service, XP002664457.
Database Registry [Online] (Apr. 13, 2007), Chemical Abstracts Service, XP002664462.
Database Registry [Online] (Nov. 10, 2004), Chemical Abstracts Service, XP002664464.

(Continued)

*Primary Examiner* — Sarah Pihonak
(74) *Attorney, Agent, or Firm* — Goodwin Procter LLP

(57) ABSTRACT

The invention provides sulphonamide compounds and their use in treating medical disorders, such as obesity. Pharmaceutical compositions and methods of making various sulphone compounds are provided. The compounds are contemplated to have activity against methionyl aminopeptidase 2.

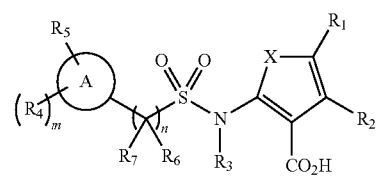

19 Claims, No Drawings

(56) References Cited

OTHER PUBLICATIONS

Database Registry [Online] (Apr. 18, 2001), Chemical Abstracts Service, XP002664465.
International Search Report for International Application No. PCT/US2011/055987, mailed Jan. 16, 2012, 6 pages.
Kawai, Megumi, et al. (2006) "Development of Sulfonamide Compounds as Potent Methionine Aminopeptidase Type II Inhibitors with Antiproliferative Properties," *Bioorganic & Medicinal Chemistry Letters*. vol. 16, pp. 3574-3577.
Sheppard, George S., et al. (2006) "Discovery and Optimization of Anthranilic Acid Sulfonamides as Inhibitors of Methionine Aminopeptidase-2: A Structural Basis for the Reduction of Albumin Binding," *J. Med. Chem*. vol. 49, pp. 3832-3849.
Shvedov, V. I, et al. (1977) "Functional Derivatives of Thiophene", *Chemistry of Heterocyclic Compounds*, vol. 13, pp. 163-165.
Wang, Jieyi, et al. (2008) "Correlation of Tumor Growth Suppression and Methionine Aminopetidase-2 Activity Blockade Using an Orally Active Inhibitor," PNAS. vol. 105(6), pp. 1838-1843.
Wang, Jieyi, et al. (2007) "Lead Optimization of Methionine Aminopeptidase-2 (MetAP2) Inhibitors Containing Sulfonamide of 5,6-disubstituted Anthranilic Acids," Bioorganic & Medicinal Chemistry Letters. vol. 17, pp. 2817-2822.
Written Opinion for International Application No. PCT/US2011/055987, mailed Jan. 16, 2012, 8 pages.
U.S. Appl. No. 14/372,877, filed Jul. 17, 2014.
U.S. Appl. No. 14/372,893, filed Jul. 17, 2014.
Hughes et al. "Ascending dose-controlled trial of beloranib, a novel obesity treatment for safety, tolerability, and weight loss in obese women" *Obesity (Silver Spring)*. Sep. 2013;21(9):1782-8. doi: 10.1002/oby.20356. Epub May 25, 2013.

* cited by examiner

SULPHONAMINE COMPOUNDS AND METHODS OF MAKING AND USING SAME

CROSS REFERENCE TO RELATED APPLICATIONS

This application is a national stage filing under 35 U.S.C. §371 of PCT/US2011/055987 filed Oct. 12, 2011 which claims priority to U.S. provisional patent application Ser. No. 61/392,108, filed Oct. 12, 2010 and U.S. provisional patent application Ser. No. 61/420,050, filed Dec. 6, 2010, all of which are hereby incorporated by reference in their entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4 S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitor, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res 63:7861) and infectious diseases such as microsporidiosis, leishmaniasis, and malaria (Zhang et al. (2002) J Biomed Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc Natl Acad Sci USA 99:10730).

Such MetAP2 inhibitors may be useful as well for patients with excess adiposity and conditions related to adiposity including type 2 diabetes, hepatic steatosis, and cardiovascular disease (via e.g. by ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The invention provides, for example, compounds which may be modulators of MetAP2, and their use as medicinal agents, processes for their preparation, pharmaceutical compositions containing them as an active ingredient both alone or in combination with other agents, to their use as medicaments and to their use in the manufacture of medicaments for the use in the inhibition of MetAP2 activity in warm-blooded animals such as humans. In particular this invention relates to compounds useful for the treatment of obesity, type 2 diabetes, and other obesity-associated conditions. Also provided are pharmaceutical compositions comprising at least one disclosed compound and a pharmaceutically acceptable carrier.

In an embodiment, provided herein are compounds represented by formula I:

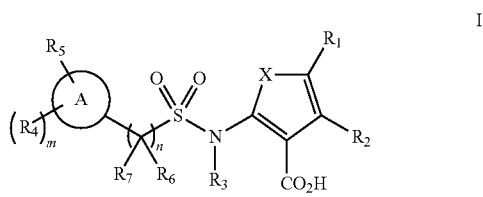

and pharmaceutically acceptable salts, stereoisomers, esters and prodrugs thereof, or pharmaceutically acceptable salts, stereoisomers, esters or prodrugs thereof, where $R_1$, $R_2$, $R_3$, X, $R_7$, $R_4$, $R_6$, $R_5$, A, n, m are as defined herein.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_{1-6}$alkoxy, and $C_2$-$C_6$alkoxy, respectively. Exemplary alkoxy groups include, but are not limited to methoxy, ethoxy, isopropoxy, etc.

The term "alkenyloxy" used herein refers to a straight or branched alkenyl group attached to an oxygen (alkenyl-O). Exemplary alkenoxy groupd include, but are not limited to, groups with an alkenyl group of 3-6 carbon atoms referred to herein as $C_{3-6}$alkenyloxy. Exemplary "alkenoxy" groups include, but are not limited to allyloxy, butenoxy, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, such as a straight or branched group of 1-6, 1-4, or 1-3 carbon atoms, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$alkynyl, and $C_3$-$C_6$alkynyl, respectively. Exemplary alkynyl groups include, but are not limited to, ethynyl, propynyl, butynyl, pentynyl, hexynyl, methylpropynyl, etc.

The term "bridged cycloalkyl", as used herein, is defined as a monocyclic 4- to 7-membered cycloalkyl group in which two non-adjacent atoms are linked by a $CH_2$ or $CH_2CH_2$ group. A "bridged cycloalkyl" may be fused to one or more phenyl, partially unsaturated, or saturated rings. Examples of bridged cycloalkyl groups include but are not limited to bicyclo[2.2.1]heptane, bicyclo[2.2.2]octane, bicyclo[2.2.2]octene etc.

The term "carbonyl" as used herein refers to the radical —C(O)—. The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or partically unsaturated hydrocarbon group of for example 3-6, or 4-6 carbons, referred to herein, e.g., as $C_{3-6}$cycloalkyl or $C_{4-6}$cycloalkyl. and derived from a cycloalkane. Exemplary cycloalkyl groups include, but are not limited to, cyclohexane, cyclohexene, cyclopentane, cyclobutane or, cyclopropane.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridyl, and pyrimidinyl.

The terms "heterocyclyl" or "heterocyclic group" are art-recognized and refer to saturated or partially unsaturated 4- to 7-membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited to pyrrolidine, piperidine, morpholine, thiomorpholine, and piperazine.

"Bridged heterocyclyl", as used herein, is defined as a saturated or partially unsaturated monocyclic 4- to 7-membered heterocyclyl group in which two non-adjacent atoms are linked by a $CH_2$ or $CH_2CH_2$ group. A "bridged heterocycle" may be fused to one or more phenyl, partially unsaturated, or saturated rings. Examples of bridged heterocyclic groups include but are not limited to 7-azabicyclo[2.2.1]heptane, 2-azabicyclo[2.2.1]heptane, 2-oxabicyclo[2.2.2]heptane, 2-oxabicyclo[2.2.2]heptene etc.

The term "heterocyclylalkoxy" as used herein refers to a heterocyclyl-alkyl-O— group.

The term "heterocyclyloxyalkyl" refers to a heterocyclyl-O-alkyl— group.

The term "heterocyclyloxy" refers to a heterocyclyl-O— group. The term "heteroaryloxy" refers to a heteroaryl-O— group.

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the invention contains an alcohol functional group, a prodrug can be formed by the replacement of the hydrogen atom of the alcohol group with a group such as $(C_1-C_6)$alkanoyloxymethyl, 1-($(C_{1-6})$alkanoyloxy)ethyl, 1-methyl-1-($(C_{1-6})$alkanoyloxy)ethyl $(C_{1-6})$alkoxycarbonyloxymethyl, N—$(C_1-C_6)$alkoxycarbonylaminomethyl, succinoyl, $(C_{1-6})$alkanoyl, α-amino$(C_{1-4})$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

I. Sulfonamide Compounds

In certain embodiments, the present invention provides compounds of formula I:

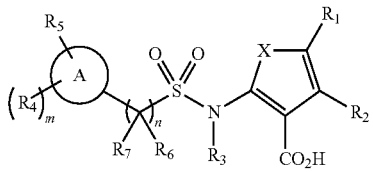

and pharmaceutically acceptable salts, stereoisomers, esters and prodrugs thereof, wherein X is selected from the group consisting of S, O, or $NR_8$;

$R_1$ is selected from the group consisting of hydrogen, halogen, cyano, $C_{1-6}$alkyl, $C_{2-6}$alkenyl, $C_{2-6}$alkynyl, $C_{3-6}$cycloalkyl, $C_{1-6}$alkoxy, $R^cR^d$—N—C(O)—, phenyl, phenyl-$C_{1-6}$alkyl-, heteroaryl, heteroaryl-$C_{1-6}$alkyl-, heterocyclyl, and heterocyclyl-$C_{1-6}$alkyl-, wherein said heteroaryl is a 5-6 membered ring having one, two or three heteroatoms selected from O, S, or N, and wherein said phenyl or heteroaryl is optionally substituted with one or more substituents selected from $R^a$; wherein said heterocyclyl is a 4-7 membered ring optionally substituted by one or more substituents selected from $R^b$ and wherein if said heterocyclyl contains a —NH moiety that nitrogen may be optionally substituted by one or more groups $R^f$; and wherein $C_{1-6}$alkyl, $C_{1-6}$alkoxy, $C_{2-6}$alkenyl, $C_{3-6}$cycloalkyl and $C_{2-6}$alkynyl may be optionally substituted by one or more substituents selected from halogen, $R^cR^dN$—, $C_1$-4alkoxy, and cyano;

$R_2$ is selected from the group consisting of hydrogen, halogen, cyano, $C_{1-6}$alkyl, $C_{2-6}$alkenyl, $C_{2-6}$alkynyl, $C_{3-6}$cycloalkyl, $C_{1-6}$alkoxy, $R^cR^d$—N—C(O)—$C_{1-6}$alkyl, phenyl, phenyl-$C_{1-6}$alkyl-, phenyl-$C_{1-6}$alkoxy-, heteroaryl, heteroaryl-$C_{1-6}$alkyl-, heteroaryl-$C_{1-6}$alkoxy-, heterocyclyl, heterocyclyl-$C_{1-6}$alkoxy, and heterocyclyl-$C_{1-6}$alkyl-, wherein said heteroaryl is a 5-6 membered ring having one, two or three heteroatoms selected from O, S, or N, and wherein said phenyl or heteroaryl is optionally substituted with one or more substituents selected from $R^a$; wherein said heterocyclyl is a 4-7 membered ring optionally substituted by one or more substituents selected from $R^b$ and wherein if said heterocyclyl contains a —NH moiety that nitrogen may be optionally substituted by one or more groups $R^f$; and wherein $C_{1-6}$alkyl, $C_{1-6}$alkoxy, $C_{2-6}$alkenyl, $C_{3-6}$cycloalkyl and $C_{2-6}$alkynyl may be optionally substituted by one or more substituents selected from halogen, hydroxyl, $R^cR^dN$—, $C_{1-4}$alkoxy, and cyano; or $R_1$ and $R_2$ may be joined together with the carbons to which they are attached to form a 5-7 membered saturated, partially unsaturated, or unsaturated ring, optionally having 1, 2 or 3 groups selected from O, $NR^f$, or S(O)$_r$ where r is 0, 1, or 2, wherein the formed 5-7 membered ring is optionally substituted on a carbon by one or more groups $R^e$, and wherein the formed ring may be optionally bridged by a moiety selected from $CH_2$, —$(CH_2)_2$—, cis-CH=CH—, $NR^f$; —O—, or —$CH_2NR^f$—;

$R_3$ is selected from the group consisting of hydrogen or $C_{1-6}$alkyl, wherein $C_{1-6}$ alkyl may be optionally substituted by one or more substituents selected from the group consisting of halogen, hydroxyl, $C_{1-6}$alkoxy, $C_{3-6}$cycloalkyl, or $R^cR^dN$—;

$R_4$ is selected from the group consisting of halogen, cyano, $C_{1-6}$alkyl, $C_{2-6}$alkenyl, $C_{2-6}$alkynyl, $C_{3-6}$cycloalkyl, $C_{1-6}$alkoxy and $R^fR^gN$—, wherein $C_{1-6}$alkyl, $C_{1-6}$alkoxy, $C_{2-6}$alkenyl, $C_{3-6}$cycloalkyl and $C_{2-6}$alkynyl may be optionally substituted by one or more halogens;

$R_5$ is selected from the group consisting of hydrogen, halogen, $C_{1-6}$alkyl, $C_{1-6}$alkoxy, $C_{2-6}$alkenyl, $C_{2-6}$alkynyl, $C_{3-6}$cycloalkyl, $C_{1-6}$alkoxy, $C_{3-6}$cycloalkyl$C_{1-6}$alkyl-, $C_{1-6}$alkyl-S(O)$_w$— wherein w is 0, 1 or 2, $C_{1-6}$ alkyl-N($R^c$)-carbonyl, $C_{1-6}$alkyl-carbonyl-N($R^c$)—, $C_{1-6}$alkyl-N($R^c$)-carbonyl-N($R^c$)—, and $C_{1-6}$ alkyl-N($R^c$)—, wherein $C_{1-6}$alkyl, $C_{1-6}$alkoxy, $C_{2-6}$alkenyl, $C_{3-6}$cycloalkyl and $C_{2-6}$alkynyl may be optionally substituted by one or more substituents selected from halogen, hydroxyl, $R^cR^dN$—, $C_{1-4}$alkoxy, $C_{1-6}$alkyl, $C_{3-6}$cycloalkyl, cyano, phenyl, heteroaryl and heterocyclyl; wherein phenyl or heteroaryl is optionally substituted with one or more substituents selected from $R^a$; wherein said heterocyclyl is a 4-7 membered ring optionally substituted by one or more substituents selected from $R^b$ and wherein if said heterocyclyl contains a —NH moiety that nitrogen may be optionally substituted by one or more groups $R^f$;

$R_6$ and $R_7$ are each independently selected from the group consisting of hydrogen, halogen, $C_{1-6}$alkyl, $C_{2-6}$alkenyl, $C_{3-6}$alkynyl, and $C_{3-6}$cycloalkyl; or $R_6$ and $R_7$ taken together with the carbon to which they are attached form a cyclopropyl ring or 4-6 membered ring which may optionally have one atom or group selected from N($R^c$), O or S(O)$_p$; wherein said ring may be optionally substituted by one or more $C_{1-6}$alkyl substituents; and wherein $C_{1-6}$alkyl, $C_{2-6}$alkenyl, $C_{3-6}$alkynyl, and $C_{3-6}$cycloalkyl may be optionally substituted by one or more substituents selected from the group consisting of halogen, hydroxyl, $R^eR^dN$—, $C_{1-4}$alkoxy, $C_{3-6}$cycloalkyl, and $C_{1-6}$alkyl;

A is a ring selected from the group consisting of phenyl, a 5-6 membered heteroaryl having 1, 2 or 3 heteroatoms selected from S, N or O, a $C_3$-$C_6$cycloalkyl, a 4-7 membered heterocycle, a bridged 6-10 membered heterocycle, and a bridged 6-10 membered cycloalkyl;

n is 0, 1, or 2;

m is 0, 1, 2, or 3;

p is 0, 1, or 2;

$R_8$ is selected from the group consisting of hydrogen, $C_{1-6}$alkyl, $C_{3-6}$alkenyl, $C_{3-6}$alkynyl, and $C_{3-6}$cycloalkyl wherein $C_{1-6}$alkyl, $C_{3-6}$alkenyl, $C_{3-6}$cycloalkyl and $C_{3-6}$alkynyl may be optionally substituted by one or more substituents selected from halogen, hydroxyl, $R^cR^dN$—, $C_{1-4}$alkoxy, $C_{3-6}$cycloalkyl, and $C_{1-6}$alkyl;

$R^a$ is independently selected, for each occurrence, from the group consisting of halogen, hydroxyl, cyano, $C_{1-6}$alkyl, $C_{3-6}$cycloalkyl, $C_{1-6}$alkoxy, $R^cR^d$Ncarbonyl, $R^cR^dN$—, $R^cR^dN$-carbonyl-$C_{1-6}$alkyl, $R^cR^dN$-carbonyl-$N(R^c)$—; $R^cR^dN$—$SO_2$—, $R^cR^dN$—$SO_2$—$N(R^c)$—; and $C_{1-6}$alkyl-carbonyl-$N(R^c)$—, wherein $C_{1-6}$alkyl, $C_{2-6}$alkoxyl, and $C_{3-6}$cycloalkyl may be optionally substituted by one or more substituents selected from halogen, hydroxyl, $R^cR^dN$—, $C_{1-4}$alkoxy, $C_{3-6}$cycloalkyl, and $C_{1-6}$alkyl;

$R^b$ is independently selected, for each occurrence, from the group consisting of halogen, hydroxyl, cyano, oxo, $C_{1-6}$alkyl, or $C_{1-6}$alkoxy, wherein $C_{1-6}$alkyl, and $C_{1-6}$alkoxy, may be optionally substituted by one or more substituents selected from halogen, hydroxyl, $C_{1-4}$alkoxy, $C_{3-6}$cycloalkyl, and $C_{1-6}$alkyl;

$R^c$ and $R^d$ independently selected, for each occurrence, from the group consisting of hydrogen or $C_{1-6}$alkyl optionally substituted by one or more halogens; or $R^c$ and $R^d$, if they occur together, may form a 4-7 membered heterocyclyl together with the nitrogen to which they are attached, which may be optionally substituted by one or more substituents selected from $R^b$;

$R^e$ is $C_{1-6}$alkyl optionally substituted by one or more halogens;

$R^f$ is independently selected from the group consisting of $C_{1-6}$alkyl, $C_{1-6}$alkylcarbonyl, or $C_{1-6}$alkylsuphonyl, wherein $C_{1-6}$alkyl, may be optionally substituted by one or more halogens.

For example, A may be phenyl or pyridinyl. In another embodiment, A may be a bridged cycloalkyl, as for example, bicyclo[2.2.1]heptanyl or a bicyclo[2.2.2]octanyl, a bridged heterocyclyl such as for example, bicyclo[2.2.1]heptane or a bicyclo[2.2.2]octane and/or such as the bridged alkyls depicted below:

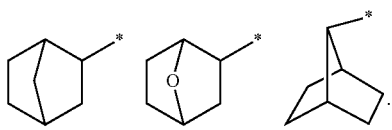

In some embodiments, X may be S or $NR_8$, for example, X may be S.

In certain embodiments, $R_3$ is H.

$R_5$, in certain embodiments, may be selected from the group consisting of hydrogen, $C_{1-6}$alkoxy, $C_{1-6}$alkyl, $C_{2-6}$alkenyl, $C_{2-6}$alkynyl, $C_{3-6}$cycloalkyl, $C_{1-6}$alkoxy, $C_{3-6}$cycloalkyl$C_{1-6}$alkyl-, $C_{1-6}$alkyl-$S(O)_w$— wherein w is 0, 1 or 2, $C_{1-6}$ alkyl-$N(R^c)$-carbonyl, $C_{1-6}$alkyl-carbonyl-$N(R^c)$—, $C_{1-6}$alkyl-$N(R^c)$-carbonyl-$N(R^c)$—, and $C_{1-6}$ alkyl-$N(R^c)$—, wherein $C_{1-6}$alkyl, $C_{1-6}$alkoxy, $C_{2-6}$alkenyl, $C_{3-6}$cycloalkyl and $C_{2-6}$alkynyl may be optionally substituted by $R^cR^dN$—.

$R_1$ may be, in certain embodiments, selected from the group consisting of $C_{1-6}$alkyl, phenyl or heteroaryl. $R_2$ may be, in certain embodiments selected from the group consisting of H, $C_{1-6}$alkyl, or $C_{1-6}$alkoxy, wherein $C_{1-6}$alkyl or $C_{1-6}$alkoxy is optionally substituted by one or more substituents selected from halogen and $R^cR^dN$—.

In some embodiments, X is S and $R_1$ and $R_2$ may be taken together with the ring to which they are attached, to form a moiety selected from the group consisting of:

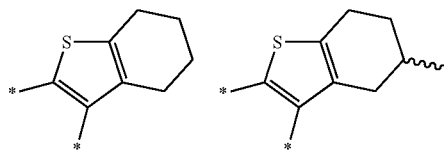

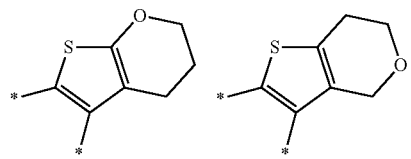

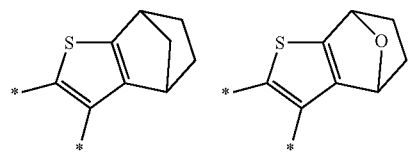

where the point of attachments relate to Formula I.

In other embodiments, $R_1$ and $R_2$ are joined together with the ring on which they are attached to from a moiety selected from:

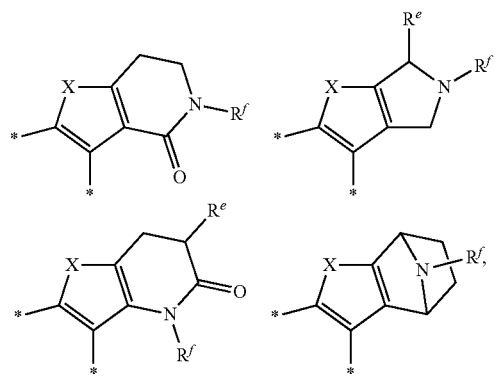

wherein $R^e$ and $R^f$ are defined above.

In certain embodiments, m is 0, or n is 0, or both m and n are 0.

For example, in one embodiment, Formula I can be represented by Ia, wherein X, $R_1$, $R_2$, $R_3$, and $R_5$ are defined above.

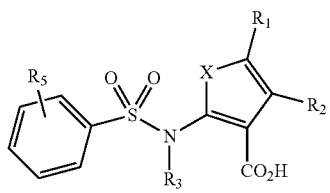

Contemplated heteroaryls, in some embodiments, include five membered heteraryls having one or two heteroatoms selected from O, N, and S, and for example, may be selected from the group consisting of furyl, thienyl, isothiazolyl, isoxazolyl, oxazolyl and pyrrolyl, e.g. may be 3-furyl or 5-isoxazolyl.

Provided herein are compounds that may be selected from the group consisting of: 2-benzenesulphonylamino-4,5,6,7-tetrahydrobenzo[b]thiophene-3-carboxylic acid, 2-(4-fluorobenzenesulphonylamino)-4,5,6,7-tetrahydrobenzo[b]thiophene-3-carboxylic acid, 2-benzenesulphonylaminobenzo[b]thiophene-3-carboxylic acid, 2-benzenesulphonylamino-5-ethyl-4-methylthiophene-3-carboxylic acid, 2-benzenesulphonylamino-4,7-dihydro-5H-thieno[2,3-c]pyran-3-carboxylic acid, 2-benzenesulphonylamino-5-phenylthiophene-3-carboxylic acid, 2-benzenesulphonylamino-4-methyl-5-phenylthiophene-3-carboxylic acid, 2-benzylsulphonylamino-4,5,6,7-tetrahydrobenzo[b]thiophene-3-carboxylic acid, 2-(2-chlorobenzenesulphonylamino)-4,5,6,7-tetrahydrobenzo[b]thiophene-3-carboxylic acid, 2-benzenesulphonylamino-5,5-dimethyl-4,5,6,7-tetrahydrobenzo[b]thiophene-3-carboxylic acid, 2-(2-methylbenzenesulphonylamino)-4,5,6,7-tetrahydrobenzo[b]thiophen-3-carboxylic acid, 2-benzenesulphonylamino-6,7-dihydro-4H-thieno[3,2-c]pyran-3-carboxylic acid, 2-benzenesulphonylamino-3,4-dihydro-2H-thieno[2,3-b]pyran-5-carboxylic acid, 2-benzenensulphonylamino-5-methyl-4,5,6,7-tetrahydrobenzo[b]thiophene-3-carboxylic acid, 2-benzenesulphonylamino-6-methyl-4,5,6,7-tetrahydrobenzo[b]thiophene-3-carboxylic acid, 2-benzenesulphonylamino-6,6-dimethyl-4,5,6,7-tetrahydrobenzo[b]thiophene-3-carboxylic acid, 2-benzenesulphonylamino-1-methyl-4,5,6,7-tetrahydro-1H-indole-3-carboxylic acid, 2-benzenesulphonylamino-5-(tetrahydropyran-4-yl)thiophene-3-carboxylic acid, 2-benzenesulphonylamino-5-ethyl-4-isopropylthiophene-3-carboxylic acid, 2-(2-trifluoromethylbenzenesulphonylamino)-4,5,6,7-tetrahydrobenzo[b]thiophene-3-carboxylic acid, 2-(2-fluorobenzenesulphonylamino)-4,5,6,7-tetrahydrobenzo[b]thiophene-3-carboxylic acid, 2-(cyclohexanesulphonylamino)-4,5,6,7-tetrahydrobenzo[b]thiophene-3-carboxylic acid, 2-(2-methoxybenzenesulphonylamino)-4,5,6,7-tetrahydrobenzo[b]thiophene-3-carboxylic acid, 2-(3-methoxybenzenensulphonylamino)-4,5,6,7-tetrahydrobenzo[b]thiophene-3-carboxylic acid, 2-(4-fluoro-2-methylbenzenesulphonylamino)-4,5,6,7-tetrahydrobenzo[b]thiophene-3-carboxylic acid, 2-benzenesulphonylamino-5-(furan-3-yl)-4-methylthiophene-3-carboxylic acid, 2-(2-ethylbenzenesulphonylamino)-4,5,6,7-tetrahydrobenzo[b]thiophene-3-carboxylic acid, 2-[2-((Z)-3-diethylaminoprop-1-enyl)benzenesulphonylamino]-4,5,6,7-tetrahydrobenzo[b]thiophene-3-carboxylic acid, 2-benzenesulphonylamino-5,6-dihydro-4H-cyclopenta[b]thiophene-3-carboxylic acid, 2-(4-chlorobenzenesulphonylamino)-4,5,6,7-tetrahydrobenzo[b]thiophene-3-carboxylic acid, 2-(3-chlorobenzenesulphonylamino)-4,5,6,7-tetrahydrobenzo[[b]thiophene-3-carboxylic acid, and pharmaceutically acceptable salts thereof and stereoisomers thereof.

Procedures for making compounds described herein are provided below with reference to Schemes 1-2. In the reactions described below, it may be necessary to protect reactive functional groups (such as hydroxy, amino, thio or carboxy groups) to avoid their unwanted participation in the reactions. The incorporation of such groups, and the methods required to introduce and remove them are known to those skilled in the art. (for example, see Greene, Wuts, *Protective Groups in Organic Synthesis*. 2nd Ed. (1999). The deprotection step may be the final step in the synthesis such that the removal of protecting groups affords a compound of Formula I, as disclosed herein Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

The strategy for the synthesis of compounds of Formula I in which X is S, as depicted in Scheme 1, generally involves forming a thiophene derivative, which can be achieved in variety of ways as exemplified below. Then, compounds of Formula I can be prepared from the intermediate by removal of any protecting groups. Specific steps in the synthetic process are described in more detail below.

SCHEME 1

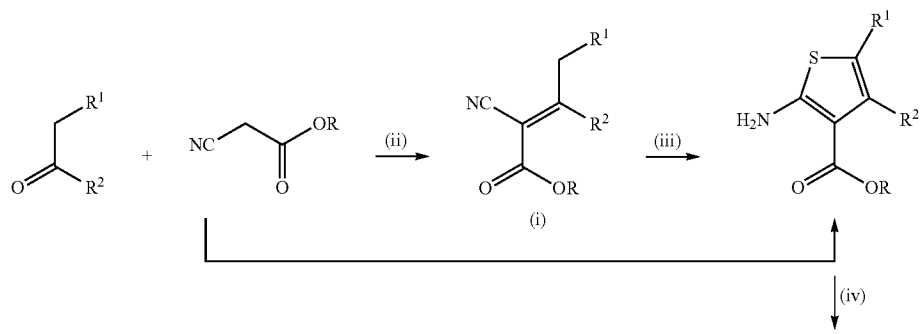

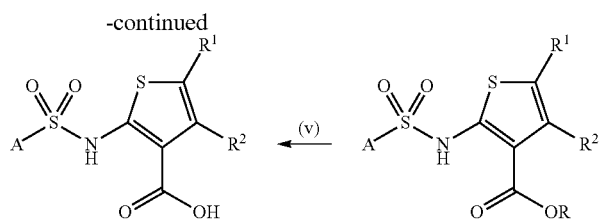

In Scheme 1, step (i) sulphur, a secondary amine such as diethylamine or morpholine in an alcohol solvent such as methanol, ethanol or isopropanol and a temperature between room temperature and the reflux temperature of the solvent is used to prepare the intermediate shown.

Alternatively, Scheme 1, step (ii) typically involves the presence of acid such as acetic acid or toluene sulphonic acid with Dean and Stark removal of water, in a solvent such as benzene or toluene at e.g., the reflux temperature of the solvent. Alternatively the reaction may be carried out in the presence of a catalyst to promote dehydration. In Scheme 1, step (iii), sulphur, a secondary amine such as diethylamine, morpholine etc in an alcohol solvent such as methanol, ethanol or isopropanol and a temperature between room temperature and the reflux temperature of the solvent is used.

Scheme 1, step (iv) typically involves the use of $ASO_2Cl$ in the presence of an organic base such as pyridine, triethylamine or N,N-di-isopropyl-N-ethylamine optionally in a solvent such as dichloromethane or toluene at a temperature between room temperature and the reflux temperature of the solvent.

Inorganic hydroxide such as lithium hydroxide or sodium hydroxide in a mixture of water and an appropriate miscible solvent such as dioxane or THF at a temperature between room temperature and the reflux temperature of the solvent or in the microwave at a temperature between 100° C. and 180° C. can be used in Scheme 1 step (v). This step can give a compound disclosed herein by the removal of any remaining protecting groups (for example, by hydrolysis of an ester to a carboxylic acid).

Alternatively compounds of Formula I in which X is S may be prepared as depicted in Scheme 2.

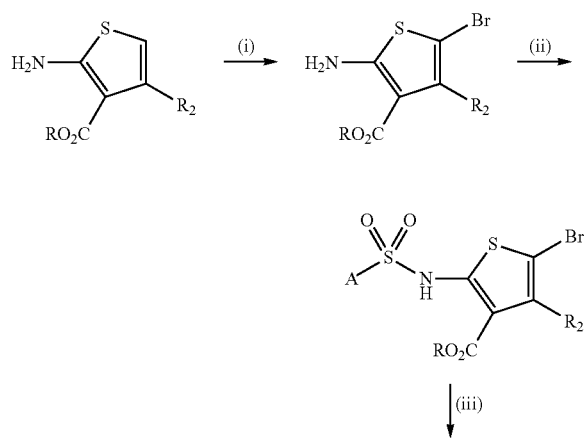

SCHEME 2

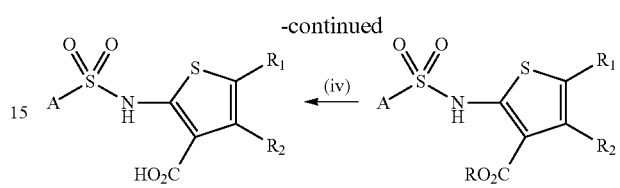

In Scheme 2, step (i) an appropriately substituted thiophene intermediate is brominated. Bromination may be carried out by treatment with a reagent such as N-bromosuccinimide or bromine in a solvent such as chloroform or dichloromethane at a temperature between 0° C. and the reflux temperature of the solvent.

Scheme 2, step (ii) typically involves the use of $ASO_2Cl$ in the presence of an organic base such as pyridine, triethylamine or N,N-di-isopropyl-N-ethylamine optionally in a solvent such as dichloromethane or toluene at a temperature between room temperature and the reflux temperature of the solvent In Scheme 2, step (iii) a carbon-carbon bond may be made by the reaction of the bromo intermediate with an organometallic reagent such as a boronic acid, or boronate ester in the presence of a palladium catalyst such as palladium chloride dppf, tetrakis-triphenylphosphine palladium (0) or bis-palladium tris(dibenzylideneacetone), in the presence of a base such as potassium carbonate or cesium carbonate in an appropriate solvent such as aqueous dioxane or aqueous tetrahydrofuran at a temperature between room temperature and the reflux temperature of the solvent or by irradiation in a microwave at a temperature between 100° C. and 160° C. for between 10 minutes and 2 hours. A wide range of appropriate reagents and conditions are known to those skilled in the art to couple organoboranes, boronates and boronic acids to bromothiophenes. [Miyaura, Suzuki, Chem. Rev. 1995, 95, 2457; Suzuki, Modern Arene Chemistry (2002), 53-106.]

Alternatively a carbon-carbon bond may be formed by the reaction of the bromo intermediate with an appropriate stannane in the presence of a palladium catalyst such as palladium chloride dppf adduct in an appropriate solvent such as dioxane, dimethoxyethane or tetrahydrofran at a temperature between room temperature and the reflux temperature of the solvent or alternatively by irradiation in the microwave at a temperature between 100° C. and 160° C. for between 10 minutes and 2 hours. A wide range of appropriate reagents and conditions are known to those skilled in the art to couple stannanes to bromothiophenes. [Smith, March, March's Advanced Organic Chemistry, 5th Edition, Wiley: New York, 2001, pp. 931-932; De Souza, Current Organic Synthesis (2006), 3(3), 313-326.]

Alternatively the carbon-carbon bond may be formed by the reaction of the bromo intermediate with an alkene (such as an acrylate) in the presence of a catalyst such as a palladium catalyst (for example tetrakis-triphenylphosphine palladium (0)) and a base or salt sucha as tributylamine or potassium acetate at a temperature between 80° C. and 120° C. or by irradiation in a microwave at a temperature between 100° C. and 160° C. for between 10 minutes and 2 hours. A wide range of appropriate reagents and conditions are known to those skilled in the art to couple alkenes to bromothiophenes. [Smith, March, *March's Advanced Organic Chemistry*, 5$^{th}$ Edition, Wiley: New York, 2001, pp. 930-931].

Alternatively the carbon-carbon bond may be formed by the reaction of the bromo intermediate with an organozinc reagent in the presence of a catalyst such as a palladium catalyst (for example tetrakis-triphenylphosphine palladium (0)) and a base or salt (such as tributylamine or potassium acetate) in an appropriate solvent such as dioxane or tetrahydrofuran at a temperature between room temperature and the reflux temperature of the solvent or by irradiation in the microwave at a temperature between 100° C. and 160° C. for between 10 minutes and 2 hours. A wide range of appropriate reagents and conditions are known to those skilled in the art to couple organozinc reagents to bromothiophenes. [Smith, March, *March's Advanced Organic Chemistry*, 5$^{th}$ Edition, Wiley: New York, 2001, pp. 540-541].

The carbon-carbon bond formed in Scheme 2, step (iii) may alternatively be prepared by the reaction of the bromo intermediate with a terminal alkyne in the presence of a palladium catalyst such as tetrakis(triphenylphosphine) palladium (0) optionally in the presence of an additional copper catalyst such as copper (I) iodide in the presence of a base or salt such as triethylamine or potassium acetate, in a solvent such as tetrahydrofuran or dimethylformamide at a temperature between room temperature and the reflux temperature of the solvent or by irradiation in the microwave at a temperature between 100° C. and 160° C. for between 10 minutes and 2 hours. A wide range of appropriate reagents and conditions are known to those skilled in the art to couple alkynes to bromothiophenes [for example, see Chinchilla, Najera, *Chemical Reviews* (2007), 107(3), 874-922].

Inorganic hydroxide such as lithium hydroxide or sodium hydroxide in a mixture of water and an appropriate miscible solvent such as dioxane or THF at a temperature between room temperature and the reflux temperature of the solvent or in the microwave at a temperature between 100° C. and 180° C. can be used in Scheme 2, step (iv). This step can give a compound disclosed herein by the removal of any remaining protecting groups (for example, by hydrolysis of an ester to a carboxylic acid).

Alternatively compounds of Formula I in which X is NR$_8$ may be prepared according to Scheme 3.

SCHEME 3

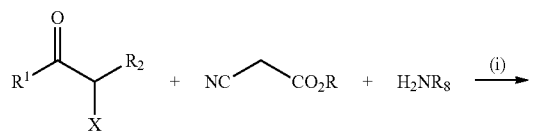

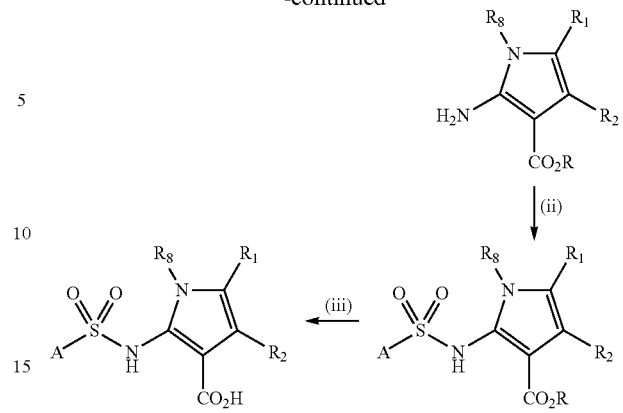

In Scheme 3, step (i) an α-haloketone is reacted with cyanoacetic ester and an appropriately substituted amine may be heated in a solvent such as dichloromethane or chloroform at a temperature between 30° C. and 100° C. to give the pyrrole intermediate shown.

Scheme 3, step (ii) typically involves the use of ASO$_2$Cl in the presence of an organic base such as pyridine, triethylamine or N,N-di-isopropyl-N-ethylamine optionally in a solvent such as dichloromethane or toluene at a temperature between room temperature and the reflux temperature of the solvent.

Inorganic hydroxide such as lithium hydroxide or sodium hydroxide in a mixture of water and an appropriate miscible solvent such as dioxane or THF at a temperature between room temperature and the reflux temperature of the solvent or in the microwave at a temperature between 100° C. and 180° C. can be used in Scheme 3, step (iii) This step can give a compound disclosed herein by the removal of any remaining protecting groups (for example, by hydrolysis of an ester to a carboxylic acid).

Alternatively step (iii) may be carried out by treatment of the ester with an acid such as trifluoroacetic acid or hydrochloric acid in a solvent such as dichloromethane or dioxane to give the compound of Formula I.

It is appreciated by one of skill in the art that, for example, that the synthetic schemes disclosed herein can be used to arrive at compounds of formula I, as described herein:

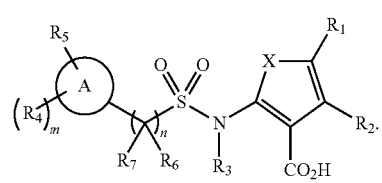

Compounds of formula I, or any of the intermediates described in the schemes above, can be further derivatised by using one or more standard synthetic methods known to those skilled in the art. Such methods can involve substitution, oxidation or reduction reactions. These methods can also be used to obtain or modify compounds of Formula I or any preceding intermediates by modifying, introducing or removing appropriate functional groups. Particular substitution approaches include alkylation, arylation, heteroarylation, acylation, thioacylation, halogenation, sulphonylation, nitration, formylation, hydrolysis and coupling procedures. These procedures can be used to introduce a functional group onto the parent molecule (such as the nitration or sulphonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl-, diisopropyl- or dimethylazodicarboxylate). Alternatively, ether groups can be prepared by deprotonation of an alcohol, using a suitable base (such as sodium hydride) followed by the addition of an alkylating agent (such as an alkyl halide or an alkylsulphonate).

In another example, a primary or secondary amine can be alkylated using a reductive alkylation process. For example, the amine can be treated with an aldehyde and a borohydride (such as sodium triacetoxyborohydride, or sodium cyanoborohydride) in a solvent (such as a halogentaed hydrocarbon, for example dichloromethane), or an alcohol, (for example ethanol) and, where necessary, in the presence of an acid (such as acetic acid).

In another example, hydroxy groups (including phenolic OH groups) can be converted into leaving groups such as halogen atoms or sulphonyloxy groups (such as alkylsulphonyloxy, for example trifluoromethylsulphonyloxy, or arylsuphonyl, for example p-toluenesulphonyloxy) using conditions known to those skilled in the art. For example, an aliphatic alcohol can be reacted with thionyl chloride in a halogenated hydrocarbon (such as dichloromethane) to afford the corresponding alkylchloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxan). Base catalysed hydrolysis can be achieved by treatment with an alkali metal hydroxide (such as lithium hydroxide (in an aqueous alcohol, (for example methanol).

In another example, aromatic halogen substituents in the compounds may be subjected to halogen-metal exchange by treatment with a base (such as a lithium base, for example n-butyl or t-butyl lithium) optionally at a low temperature (such as −78° C.) in a solvent (such as tetrahydrofuran) and then quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as the Dess-Martin reagent) in a solvent (such as a halogenated hydrocarbon, for example dichloromethane). Alternative oxidising conditions can be used, such as treatment with oxalyl chloride and an activating amount of dimethylsulphoxide and subsequent quenching by the addition of an amine (such as triethylamine). Such a reaction can be carried out in an appropriate solvent (such as a halogentaed hydrocarbon, for example dichloromethane) and under appropriate conditions (such as cooling below room temperature, for example to −78° C. followed by warming to room temperature). In another example, sulphur atoms can be oxidised to the corresponding sulphoxide or sulphone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups, saturation (or partial saturation) of unsaturated compounds including aromatic rings. For example, primary alcohols can be generated from the corresponding ester or aldehyde by reduction, using a metal hydride (such as lithium aluminium hydride or sodium sodium borohydride in a solvent such as methanol). Alternatively, —OH groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as tin or iron) in the presence of an acid (such as hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions such as cooling to below room temperature, (for example to −78° C.), or heating, (for example to reflux).

Salts of compounds of Formula I can be prepared by the reaction of a compound of Formula I with an appropriate acid or base in a suitable solvent, or mixture of solvents (such as an ether, for example, diethylether, or an alcohol, for example ethanol, or an aqueous solvent) using conventional procedures. Salts of compound of Formula I can be exchanged for other salts by treatment using conventional ion-exchange chromatography procedures.

Where it is desired to obtain a particular enantiomer of a compound of Formula I, this may be produced from a corresponding mixture of enantiomers by employing any suitable conventional procedure for resolving enantiomers. For example, diasteromeric derivatives (such as salts) can be produced by reaction of a mixture of enantiomers of a compound of General Formula I (such a racemate) and an appropriate chiral compound (such as a chiral base). The diasteromers can then be separated by any conventional means such as crystallisation) and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel *Steroselective Biocatalysts*, Marcel Decker; New York 2000).

In another resolution process a racemate of compounds of Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

II. Methods

Another aspect of the invention provides methods of modulating the activity of MetAP2. Such methods comprise exposing said receptor to a compound described herein. In some embodiments, the compound utilized by one or more of the foregoing methods is one of the generic, subgeneric, or specific compounds described herein, such as a compound of formula I. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, the invention provides a method of treating and or ameliorating obesity in a patient by administering an effective amount of a disclosed compound. Also provided herein are methods for inducing weight loss in a patient in need thereof.

Other contemplated methods of treatment include method of treating or amelioriating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the invention provides a method of treating the above medical indications comprising administering to a subject in need thereof a therapeutically effective amount of a compound described herein, such as a compound of formula I.

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$(m$^2$) (SI) or 703× weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds of the present invention also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the invention provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of formula I.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. ower dose sufficient to weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may bemixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the invention also provides kits for use by a e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc.

Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol.

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497):1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9): 978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7): 824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectra were recorded at ambient temperature using a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet. d=doublet, dd=double doublet, dt=double triplet, tt=triple triplet, t=triplet, q=quartet, m=multiplet.

Mass Spectrometry (LCMS) experiments to determine retention times (r/t) and associated mass ions were performed using the following methods:

Method A: Experiments were performed on a Micromass Platform LCT spectrometer with positive ion electrospray and single wavelength UV 254 nm detection using a Higgins Clipeus C18 5 µm 100×3.0 mm column and a 2 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Method B: Experiments were performed on a Waters Micromass ZQ2000 quadrapole mass spectrometer with positive ion and negative ion mode electrospray and single wavelength UV 254 nm detection using a Higgins Clipeus C18 5 µm 100×3.0 mm column and a 1 ml/minute flow rate. The initial solvent system was 85% water containing 0.1% formic acid (solvent A) and 15% methanol containing 0.1% formic acid (solvent B) for the first minute followed by a gradient up to 5% solvent A and 95% solvent B over the next 12 minutes. The final solvent system was held constant for a further 7 minutes.

Method C: Experiments were performed on a Waters Micromass ZQ2000 quadrapole mass spectrometer linked to a Waters Acquity UPLC system with a PDA UV detector. The spectrometer has an electrospray source operating in positive and negative ion mode and single wavelength UV 254 nm detection using a Acquity BEH C18 1.7 µm or Acquity BEH Shield RP18 1.7 µm and a 0.4 ml/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 6 minutes. The final solvent system was held constant for a further 0.8 minutes.

Method D: Experiments were performed on a Waters Micro triple quadrupole mass spectrometer linked to a Hewlett Packard HP1100 LC system with a DAD UV detector. The spectrometer has an electrospray source operating in positive and negative ion mode and DAD/ELS detection using a Higgins Clipeus C18 100×3.0 mm column and a 1 ml/minute flow rate. The solvent system was 85% water containing 0.1% formic acid (solvent A) and 15% methanol containing 0.1% formic acid (solvent B) for the first minute followed by a gradient up to 5% solvent A and 95% solvent B over the next 12 minutes. The final solvent system was held constant for a further 7 minutes.

Method E: Experiments were performed on a Micromass Platform LC spectrometer with positive and negative ion electrospray and ELS/Diode array detection using a Phenomenex Luna C18(2) 30×4.6 mm column and a 2 ml/minute flow rate. The solvent system was 95% water containing 0.1% formic acid (solvent A) and 5% methanol containing 0.1% formic acid (solvent B) for the first 0.50 minutes followed by a gradient up to 5% solvent A and 95% solvent B over the next 4 minutes. The final solvent system was held constant for a further 0.50 minutes.

Method F: Experiments were performed on a Waters ZMD quadrapole mass spectrometer with an electrospray source operating in positive and negative ion mode and ELS/Diode array detection using a Phenomenex Luna C18(2) 30×4.6 mm column and a 2 ml/minute flow rate or equivalent. The solvent system was 95% water containing 0.1% formic acid (solvent A) and 5% methanol containing 0.1% formic acid (solvent B) for the first 0.50 minutes followed by a gradient up to 5% solvent A and 95% solvent B over the next 4 minutes. The final solvent system was held constant for a further 1 minute.

Microwave experiments were carried out using a Biotage Initiator™, which uses a single-mode resonator and dynamic field tuning, both of which give reproducibility and control. Temperatures from 40-250° C. can be achieved, and pressures of up to 20 bars can be reached. Three types of vial are available for this processor, 0.5-2.0 ml, 2.0-5.0 ml and 5.0-20 ml.

Preparative HPLC purification was carried out using either a C18-reverse-phase column from Genesis (C18) or a C6-phenyl column from Phenomenex (C6 phenyl) (each have 100×22.5 mm i.d. with 7 µm particle size, UV detection at 230 or 254 nm, flow 5-15 ml/min), eluting with gradients from 100-0 to 0-100% water/acetonitrile or water/methanol containing 0.1% formic acid, with a flow rate of 18 ml/minute. Fractions containing the required product (identified by LCMS analysis) were pooled, the organic fraction was removed by evaporation, and the remaining aqueous fraction was lyophilised, to give the product.

Compounds which required column chromatography were purified manually or fully automatically using either a Biotage SP1™ Flash Purification system with Touch Logic Control™ or a Combiflash Companion® with pre-packed silica gel Isolute® SPE cartridges, Biotage SNAP cartridges or Redisep® Rf cartridges respectively.

Abbreviations: THF: Tetrahydrofuran; DMF: N,N-Dimethylformamide; DCM: Dichloromethane; Dppf: diphenylphosphino ferrocene; AIBN: Azo-bis-(isobutyronitrile) IMS: Industrial methylated spirit (95%) ethanol).

Compounds have been named using Autonom 2000 in ISISdraw

Example 1

2-Benzenesulphonylamino-4,5,6,7-tetrahydrobenzo[b]thiophene-3-carboxylic acid

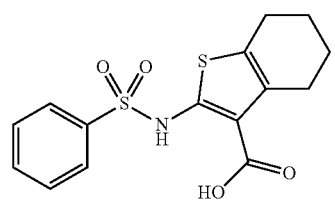 [SMILES: O=C(O)c1c(NS(=O)(=O)c2ccccc2)sc2c1CCCC2]

A solution of potassium trimethylsilanoate (0.141 g) in dry THF (5 ml) was added to a cooled solution of ethyl 2-benzenesulphonylamino-4,5,6,7-tetrahydro-benzo[b]thiophene-3-carboxylate (Intermediate 1, 0.076 g) in dry THF (5 ml). The resultant cloudy solution was stirred at room temperature for 2 hours. Further potassium trimethylsilanoate (0.076 g) was added and the resultant mixture was stirred for a total of 72 hours. The mixture was then stirred and heated at 60° C. for a total of 48 hours. The resultant mixture was diluted with water and acidified to pH1 by addition of concentrated hydrochloric acid and extracted with ethyl acetate. The organic phase was washed with water, dried (MgSO$_4$) and filtered. The filtrate was evaporated to dryness and the residue was triturated with ether. The solid was collected by filtration and air dried to give 2-benzenesulphonylamino-4,5,6,7-tetrahydrobenzo[b]thiophene-3-carboxylic acid (0.034 g) as an off white solid.

NMR (DMSO-d$_6$) δ 12.0-10.8 (br s, 1H), 7.8 (d, 2H), 7.6 (m, 1H), 7.55 (m, 2H), 2.6 (m, 2H), 2.55 (m, 2H), 1.65 (m, 4H).

LCMS (Method B): r/t 11.45 (M+H) 338, (M+Na) 360, (M−H) 336.

Example 2

2-(4-Fluorobenzenesulphonylamino)-4,5,6,7-tetrahydrobenzo[b]thiophene-3-carboxylic acid

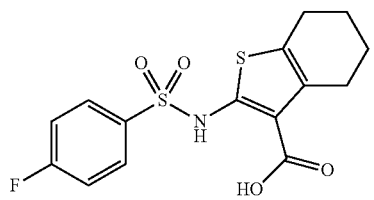 [SMILES: O=C(O)c1c(NS(=O)(=O)c2ccc(F)cc2)sc2c1CCCC2]

A solution of ethyl 2-(4-fluorobenzenesulphonylamino)-4,5,6,7-tetrahydro-benzo[b]thiophene-3-carboxylate (Intermediate 2, 0.12 g) and lithium hydroxide monohydrate (0.036 g) in a mixture of dioxane and water (2:1, 6 ml) was divided between two 2-5 ml microwave vials and the contents of each vial were stirred and heated in the microwave at 120° C. for 30 minutes. The two batches were combined, diluted with water and extracted with ethyl acetate. The aqueous phase was acidified to pH1 by addition of hydrochloric acid (1M) and the resultant suspension was extracted with ethyl acetate, washed with water, dried (MgSO$_4$) and filtered. The filtrate was evaporated to dryness and the residue was purified by chromatography on silica eluting with a mixture of methanol and DCM (2.5%) to give a solid which was triturated with DCM. The resultant solid was collected by filtration to give 2-(4-fluorobenzenesulphonylamino)-4,5,6,7-tetrahydrobenzo[b]thiophene-3-carboxylic acid (0.024 g) as a light orange solid.

NMR (DMSO-d$_6$) δ 11.5-10.5 (br s, 1H), 7.9 (m, 2H), 7.45 (m, 2H), 2.55 (m, 4H), 1.7 (m, 4H).

LCMS (Method D): r/t 11.82 (M+Na) 378.

Example 3

2-Benzenesulphonylaminobenzo[b]thiophene-3-carboxylic acid

Prepared by proceeding in a similar manner to Example 2, starting from ethyl 2-benzenesulphonylaminobenzo[b]thiophene-3-carboxylate (Intermediate 3)

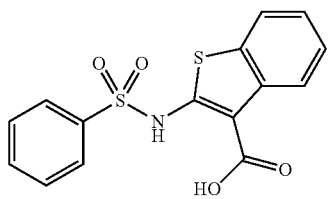 [SMILES: O=C(O)c1c(NS(=O)(=O)c2ccccc2)sc2ccccc12]

NMR (DMSO-d$_6$) δ 8.2 (d, 1H), 7.9 (d, 2H), 7.8 (d, 1H), 7.6 (m, 3H), 7.35 (t, 1H), 7.25 (t, 1H)

LCMS (Method D): r/t 11.22 (M+Na) 356

Example 4

2-Benzenesulphonylamino-5-ethyl-4-methylthiophene-3-carboxylic acid

Prepared by proceeding in a similar manner to Example 2, starting from methyl 2-benzenesulphonylamino-5-ethyl-4-methylthiophene-3-carboxylate (Intermediate 5)

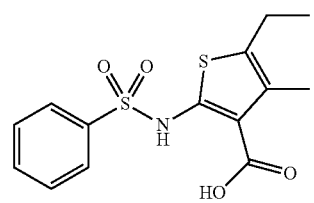 [SMILES: CCc1sc(NS(=O)(=O)c2ccccc2)c(C(=O)O)c1C]

NMR (DMSO-d$_6$) δ 11.3-10.0 (br s, 1H), 7.8 (d, 2H), 7.7 (m, 1H), 7.55 (t, 2H), 2.6 (q, 2H), 2.2 (s, 3H), 0.9 (t, 3H).

LCMS (Method D): r/t 10.98 (M+Na) 348.

Example 5

2-Benzenesulphonylamino-4,7-dihydro-5H-thieno[2,3-c]pyran-3-carboxylic acid

Prepared by proceeding in a similar manner to Example 2, starting from ethyl 2-benzenesulphonylamino-4,7-dihydro-5H-thieno[2,3-c]pyran-3-carboxylate (Intermediate 6)

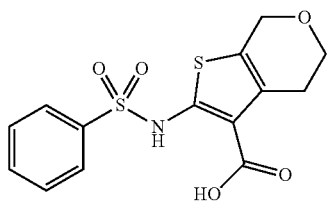 [SMILES: O=C(O)c1c(NS(=O)(=O)c2ccccc2)sc2c1CCOC2]

NMR (DMSO-d$_6$) δ 10.8 (br s, 1H), 7.8 (d, 2H), 7.7 (t, 1H), 7.6 (t, 2H), 4.55 (s, 2H), 3.8 (t, 2H), 2.7 (t, 2H)

LCMS (Method D): r/t 9.21 (M+H) 340

Example 6

2-Benzenesulphonylamino-5-phenylthiophene-3-carboxylic acid

Prepared by proceeding in a similar manner to Example 2, starting from ethyl 2-benzenesulphonylamino-5-phenylthiophene-3-carboxylate (Intermediate 8)

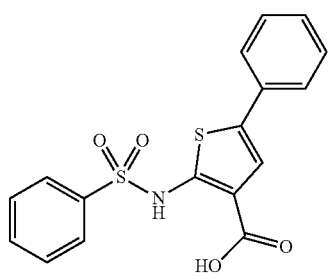 [SMILES: O=C(O)c1cc(-c2ccccc2)sc1NS(=O)(=O)c1ccccc1]

NMR (DMSO-d$_6$) δ 10.5 (br s, 1H), 7.9 (d, 2H), 7.7 (t, 1H), 7.6 (m, 4H), 7.45 (s, 1H), 7.4 (t, 2H), 7.3 (t, 1H)
LCMS (Method D): r/t 11.90 (M+H) 360

Example 7

2-Benzenesulphonylamino-4-methyl-5-phenylthiophene-3-carboxylic acid

Prepared by proceeding in a similar manner to Example 2, starting from methyl 2-benzenesulphonylamino-4-methyl-5-phenylthiophene-3-carboxylate (Intermediate 9)

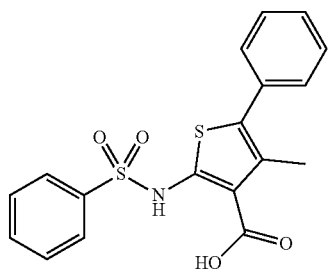 [SMILES: Cc1c(-c2ccccc2)sc(NS(=O)(=O)c2ccccc2)c1C(=O)O]

NMR (DMSO-d$_6$) δ 11.5-10.5 (br s, 1H), 7.9 (d, 2H), 7.7 (t, 1H), 7.6 (t, 2H), 7.45 (t, 2H), 7.4 (m, 3H), 2.2 (s, 3H)
LCMS (Method D): r/t 12.15 (M+H) 374, (M+Na) 396

Example 8

2-Phenylmethanesulphonylamino-4,5,6,7-tetrahydrobenzo[b]thiophene-3-carboxylic acid Prepared by proceeding in a similar manner to Example 2, starting from ethyl 2-phenylmethanesulphonylamino-4,5,6,7-tetrahydrobenzo[b]thiophene-3-carboxylate (Intermediate 10)

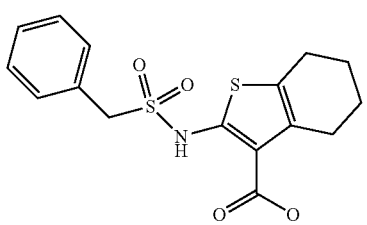 [SMILES: O=C(O)c1c(NS(=O)(=O)Cc2ccccc2)sc2c1CCCC2]

NMR (DMSO-d$_6$) δ 10.6 (br s, 1H), 7.4-7.3 (m, 5H), 4.55 (s, 2H), 2.7 (m, 2H), 2.55 (m, 2H), 1.65 (m, 4H).
LCMS (Method D): r/t 11.73 (M+Na) 374.

Example 9

2-(2-Chlorobenzenesulphonylamino)-4,5,6,7-tetrahydrobenzo[b]thiophene-3-carboxylic acid Prepared by proceeding in a similar manner to Example 2, starting from ethyl 2-(2-chlorobenzenesulphonylamino)-4,5,6,7-tetrahydrobenzo[b]thiophene-3-carboxylate (Intermediate 11)

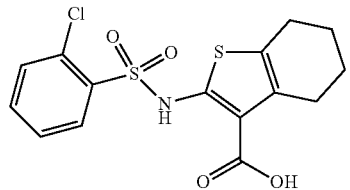 [SMILES: O=C(O)c1c(NS(=O)(=O)c2ccccc2Cl)sc2c1CCCC2]

NMR (DMSO-d$_6$) δ 11.5 (br s, 1H), 8.05 (m, 1H), 7.7 (m, 2H), 7.6 (m, 1H), 2.6 (m, 2H), 2.5 (m, 2H), 1.65 (m, 4H).
LCMS (Method D): r/t 11.91 (M+H) 372.

Example 10

2-Benzenesulphonylamino-5,5-dimethyl-4,5,6,7-tetrahydrobenzo[b]thiophene-3-carboxylic acid Prepared by proceeding in a similar manner to Example 2, starting from ethyl 2-benzenensulphonylamino-5,5-dimethyl-4,5,6,7-tetrahydrobenzo[b]thiophene-3-carboxylate (Intermediate 12)

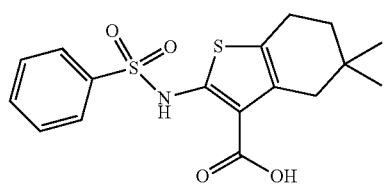 [SMILES: CC1(C)CCc2sc(NS(=O)(=O)c3ccccc3)c(C(=O)O)c2C1]

NMR (DMSO-d$_6$) δ 11.15 (br s, 1H), 7.8 (m, 2H), 7.65 (m, 1H), 7.6 (m, 2H), 2.5 (t, 2H), 2.4 (m, 2H), 1.5 (t, 2H), 1.9 (s, 6H).
LCMS (Method D): r/t 12.37 (M+H) 366.

Example 11

2-(2-Methylbenzenesulphonylamino)-4,5,6,7-tetrahydrobenzo[b]thiophen-3-carboxylic acid Prepared by proceeding in a similar manner to Example 2, starting from ethyl 2-(2-methylbenzenensulphonylamino)-4,5,6,7-tetrahydrobenzo[b]thiophen-3-carboxylate (Intermediate 13)

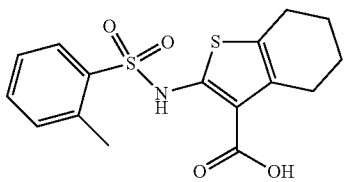 [SMILES: Cc1ccccc1S(=O)(=O)Nc1sc2c(c1C(=O)O)CCCC2]

NMR (DMSO-d$_6$) δ 10.5 (br s, 1H), 8.05 (m, 1H), 7.5 (m, 1H), 7.3 (m, 2H), 2.75 (m, 2H), 2.7 (s, 3H), 2.5 (m, 2H), 1.75 (m, 4H).
LCMS (Method D): r/t 4.19 (M+Na) 374.

Example 12

2-Benzenesulphonylamino-6,7-dihydro-4H-thieno[3,2-c]pyran-3-carboxylic acid

Prepared by proceeding in a similar manner to Example 2, starting from a mixture of methyl 2-benzenesulphonylamino-6,7-dihydro-4H-thieno[3,2-c]pyran-3-carboxylate and methyl 2-[bis-(benzenesulphonyl)amino]-6,7-dihydro-4H-thieno[3,2-c]pyran-3-carboxylate (Intermediate 14)

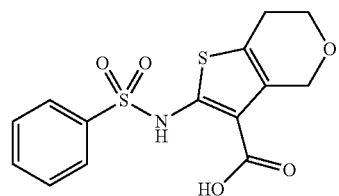 [SMILES: O=C(O)c1c(NS(=O)(=O)c2ccccc2)sc2c1COCC2]

NMR (DMSO-d$_6$) δ 11.4-10.4 (br s, 1H), 7.85 (d, 2H), 7.65 (t, 1H), 7.6 (t, 2H), 4.55 (s, 2H), 3.8 (t, 2H), 2.65 (t, 2H)
LCMS (Method D): r/t 9.36 (M+Na) 362.

Example 13

2-Benzenesulphonylamino-3,4-dihydro-2H-thieno[2,3-b]pyran-5-carboxylic acid

Prepared by proceeding in a similar manner to Example 2, starting from methyl 2-benzenesulphonylamino-3,4-dihydro-2H-thieno[2,3-b]pyran-5-carboxylate (Intermediate 15)

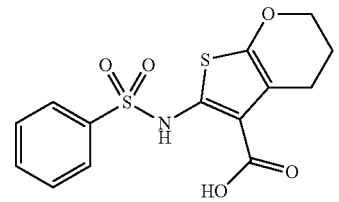 [SMILES: O=C(O)c1c(NS(=O)(=O)c2ccccc2)sc2c1CCCO2]

NMR (DMSO-d$_6$) δ 7.8 (d, 2H), 7.7 (t, 1H), 7.6 (t, 2H), 4.15 (m, 2H), 2.55 (t, 2H), 1.85 (m, 2H)
LCMS (Method D): r/t 10.19 (M+Na) 362

Example 14

2-Benzenensulphonylamino-5-methyl-4,5,6,7-tetrahydrobenzo[b]thiophene-3-carboxylic acid Prepared by proceeding in a similar manner to Example 2, starting from ethyl 2-benzenesulphonylamino-5-methyl-4,5,6,7-tetrahydrobenzo[b]thiophene-3-carboxylate (Intermediate 18)

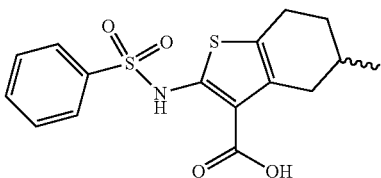 [SMILES: CC1CCc2sc(NS(=O)(=O)c3ccccc3)c(C(=O)O)c2C1]

NMR (DMSO-d$_6$) δ 11.25 (br s, 1H), 7.8 (m, 2H), 7.65 (m, 1H), 7.6 (m, 2H), 2.8 (m, 1H), 2.55 (m, 2H), 2.05 (m, 1H), 1.8 (m, 1H), 1.7 (m, 1H), 1.3 (m, 1H), 1.0 (d, 3H). LCMS (Method D): r/t 12.07 (M+Na) 374.

Example 15

2-Benzenesulphonylamino-6-methyl-4,5,6,7-tetrahydrobenzo[b]thiophene-3-carboxylic acid Prepared by proceeding in a similar manner to Example 2, starting from ethyl 2-benzenesulphonylamino-6-methyl-4,5,6,7-tetrahydrobenzo[b]thiophene-3-carboxylate (Intermediate 19)

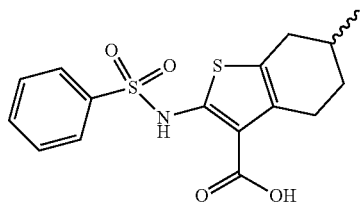 [SMILES: CC1CCc2c(sc(NS(=O)(=O)c3ccccc3)c2C(=O)O)C1]

NMR (DMSO-d$_6$) δ 11.05 (br s, 1H), 7.8 (m, 2H), 7.65 (m, 1H), 7.6 (m, 2H), 2.75 (m, 1H), 2.65 (m, 1H), 2.45 (m, 1H), 2.15 (m, 1H), 1.75 (m, 2H), 1.25 (m, 1H), 1.0 (d, 3H).
LCMS (Method D): r/t 12.20 (M+H) 352.

Example 16

2-Benzenesulphonylamino-6,6-dimethyl-4,5,6,7-tetrahydrobenzo[b]thiophene-3-carboxylic acid Prepared by proceeding in a similar manner to Example 2, starting from ethyl 2-benzenesulphonylamino-6,6-dimethyl-4,5,6,7-tetrahydrobenzo[b]thiophene-3-carboxylate (Intermediate 20).

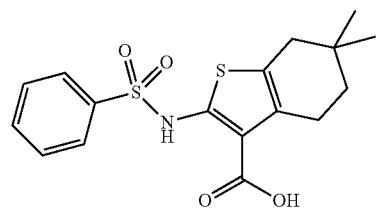 [SMILES: CC1(C)CCc2c(sc(NS(=O)(=O)c3ccccc3)c2C(=O)O)C1]

NMR (DMSO-d$_6$) δ 11.05 (br s, 1H), 7.8 (m, 2H), 7.7 (m, 1H), 7.6 (m, 2H), 2.6 (t, 2H), 2.35 (m, 2H), 1.4 (t, 2H), 0.9 (s, 6H).
LCMS (Method D): r/t 12.48 (M+H) 366.

Example 17

2-Benzenesulphonylamino-1-methyl-4,5,6,7-tetrahydro-1H-indole-3-carboxylic acid

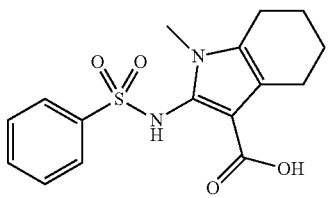 [SMILES: Cn1c2c(c(C(=O)O)c1NS(=O)(=O)c1ccccc1)CCCC2]

tert-Butyl 2-benzenesulphonylamino-1-methyl-4,5,6,7-tetrahydro-1H-indole-3-carboxylate (Intermediate 21, 0.3 g) was added to HCl in dioxane (4M, 3.8 ml) at 0° C. The cold bath was removed and the mixture was allowed to warm to room temperature and then stirred for 2 hours. The mixture was cooled to 0° C. and neutralised with saturated aqueous sodium bicarbonate solution. The mixture was extracted with ethyl acetate, washed with brine, dried (MgSO$_4$) and filtered. The filtrate was evaporated to dryness and the residue was triturated with DCM (15 ml). The solid was collected by filtration and triturated with hot ethyl acetate (3 ml). The solid was collected by filtration and air dried to afford 2-benzenesulphonylamino-1-methyl-4,5,6,7-tetrahydro-1H-indole-3-carboxylic acid (0.017 g) as a white solid.

NMR (DMSO-d$_6$) δ 11.2 (br s, 2H), 7.65-7.6 (m, 3H), 7.55 (t, 2H), 3.15 (s, 3H), 2.5 (m, 2H), 2.45 (m, 2H), 1.65 (m, 4H)
LCMS (Method D): r/t 9.04 (M+Na) 357.

Example 18

2-Benzenesulphonylamino-5-(tetrahydropyran-4-yl)thiophene-3-carboxylic acid

Prepared by proceeding in a similar manner to Example 2, starting from ethyl 2-benzenesulphonylamino-5-(tetrahydropyran-4-yl)thiophene-3-carboxylate (Intermediate 23)

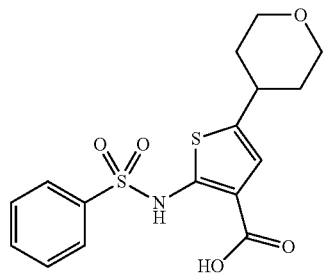 [SMILES: O=C(O)c1cc(C2CCOCC2)sc1NS(=O)(=O)c1ccccc1]

NMR (DMSO-d$_6$) δ 10.6 (br s, 1H), 7.85 (d, 2H), 7.7 (t, 1H), 7.6 (t, 2H), 6.75 (s, 1H), 3.9 (m, 2H), 3.4 (m, 2H), 2.9 (m, 1H), 1.8 (m, 2H), 1.5 (m, 2H).
LCMS (Method D): r/t 9.69 (M−H) 366.

Example 19

2-Benzenesulphonylamino-5-ethyl-4-isopropylthiophene-3-carboxylic acid

Prepared by proceeding in a similar manner to Example 2, starting from methyl 2-benzenesulphonylamino-5-ethyl-4-isopropylthiophene-3-carboxylate (Intermediate 24)

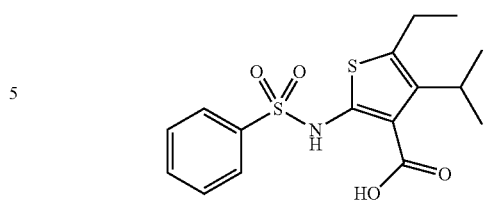

NMR (DMSO-d$_6$) δ 10.8-10.2 (br s, 1H), 7.8 (d, 2H), 7.7 (t, 1H), 7.6 (t, 2H), 3.3 (m, 1H), 2.7 (q, 2H), 1.2 (d, 6H), 1.1 (t, 3H)
LCMS (Method D): r/t 11.64 (M+Na) 376

Example 20

2-(2-Trifluoromethylbenzenesulphonylamino)-4,5,6,7-tetrahydrobenzo[b]thiophene-3-carboxylic acid

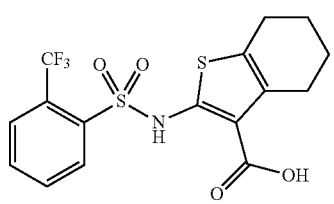 [SMILES: O=C(O)c1c(NS(=O)(=O)c2ccccc2C(F)(F)F)sc2c1CCCC2]

Lithium hydroxide monohydrate (0.188 g) was added to a solution of ethyl 2-(2-trifluoromethylbenzenesulphonylamino)-4,5,6,7-tetrahydrobenzo[b]thiophene-3-carboxylate (Intermediate 27, 0.194 g) in dioxane (1 ml) and water (1 ml) and the mixture was stirred at room temperature for 16 hours. The mixture was then warmed to 60° C. for 1 hour and finally heated in the microwave at 160° C. for 15 minutes. After cooling to room temperature the volatile components were removed under reduced pressure. The residual solution was acidified with aqueous hydrochloric acid (1M) and directly purified by preparative HPLC(C18), eluting with a mixture of methanol and water containing 0.1% formic acid and a gradient of 40-95% to give 2-(2-trifluoromethylbenzenesulphonylamino)-4,5,6,7-tetrahydrobenzo[b]thiophene-3-carboxylic acid (0.015 g) as a white solid.

NMR (DMSO-d$_6$) δ 12.0 (br s, 1H), 8.15 (d, 1H), 7.95 (d, 1H), 7.85 (m, 2H), 2.6 (m, 2H), 2.5 (m, 2H), 1.65 (m, 4H).
LCMS (Method D): r/t 11.95 (M+H) 406.

Example 21

2-(2-Fluorobenzenesulphonylamino)-4,5,6,7-tetrahydrobenzo[b]thiophene-3-carboxylic acid Prepared by proceeding in a similar manner to Example 2, starting from ethyl 2-(2-fluorobenzenesulphonylamino)-4,5,6,7-tetrahydrobenzo[b]thiophene-3-carboxylate (Intermediate 28)

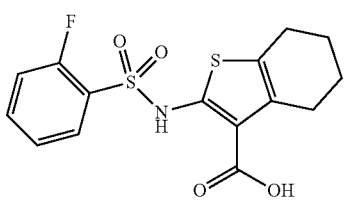 [SMILES: O=C(O)c1c(NS(=O)(=O)c2ccccc2F)sc2c1CCCC2]

NMR (DMSO-d$_6$) δ 11.55 (br s, 1H), 7.85 (m, 1H), 7.7 (m, 1H), 7.5-7.4 (m, 2H), 2.6 (m, 2H), 2.5 (m, 2H), 1.65 (m, 4H).

LCMS (Method D): r/t 11.47 (M+H) 356.

Example 22

2-(Cyclohexanesulphonylamino)-4,5,6,7-tetrahydrobenzo[b]thiophene-3-carboxylic acid Prepared by proceeding in a similar manner to Example 2, starting from ethyl 2-(cyclohexanesulphonylamino)-4,5,6,7-tetrahydrobenzo[b]thiophene-3-carboxylate (Intermediate 29)

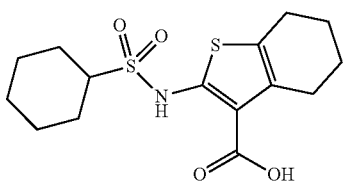 [SMILES: O=C(O)c1c(NS(=O)(=O)C2CCCCC2)sc2c1CCCC2]

NMR (DMSO-d$_6$) δ 2.9 (m, 1H), 2.65 (m, 2H), 1.95 (m, 2H), 1.9-1.65 (m, 6H), 1.6 (m, 2H), 1.4-1.0 (m, 6H).

LCMS (Method D): r/t 12.38 (M+Na) 366.

Example 23

2-(2-Methoxybenzenesulphonylamino)-4,5,6,7-tetrahydrobenzo[b]thiophene-3-carboxylic acid Prepared by proceeding in a similar manner to Example 2, starting from ethyl 2-(2-methoxybenzenesulphonylamino)-4,5,6,7-tetrahydrobenzo[b]thiophene-3-carboxylate (Intermediate 30).

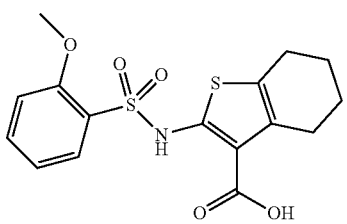 [SMILES: COc1ccccc1S(=O)(=O)Nc1sc2c(c1C(=O)O)CCCC2]

NMR (DMSO-d$_6$) δ 11.2 (br s, 1H), 7.8 (m, 1H), 7.65 (m, 1H), 7.25 (m 1H), 7.1 (m, 1H), 3.9 (s, 3H), 2.6 (m, 2H), 2.5 (m, 2H), 1.65 (m, 4H).

LCMS (Method D): r/t 11.60 (M+H) 368.

Example 24

2-(3-Methoxybenzenensulphonylamino)-4,5,6,7-tetrahydrobenzo[b]thiophene-3-carboxylic acid Prepared by proceeding in a similar manner to Example 2, starting from ethyl 2-(3-methoxybenzenesulphonylamino-4,5,6,7-tetrahydrobenzo[b]thiophene-3-carboxylate (Intermediate 31)

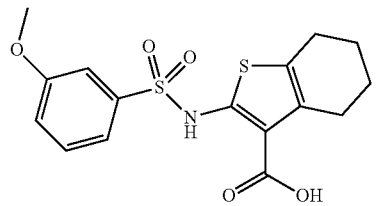 [SMILES: COc1cccc(S(=O)(=O)Nc2sc3c(c2C(=O)O)CCCC3)c1]

NMR (DMSO-d$_6$) δ 11.05 (br s, 1H), 7.5 (m, 1H), 7.35 (m, 1H), 7.3 (m, 1H), 7.25 (m, 1H), 3.8 (s, 3H), 2.55 (m, 4H), 1.7 (m, 4H).

LCMS (Method D): r/t 11.78 (M+H) 368.

Example 25

2-(4-Fluoro-2-methylbenzenesulphonylamino)-4,5,6,7-tetrahydrobenzo[b]thiophene-3-carboxylic acid Prepared by proceeding in a similar manner to Example 2, starting from a 2:1 mixture of ethyl 2-(4-fluoro-2-methylbenzenesulphonylamino)-4,5,6,7-tetrahydro-benzo[b]thiophene-3-carboxylate and ethyl 2-[bis-(4-fluoro-2-methyl-benzenesulphonyl)amino]-4,5,6,7-tetrahydrobenzo[b]thiophene-3-carboxylate (Intermediate 32)

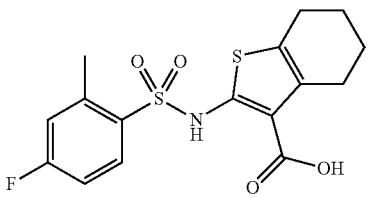 [SMILES: Cc1cc(F)ccc1S(=O)(=O)Nc1sc2c(c1C(=O)O)CCCC2]

NMR (DMSO-d$_6$) δ 11.35 (br s, 1H), 7.9 (dd, 1H), 7.3 (dd, 1H), 7.25 (dt, 1H), 2.6 (m, 5H), 2.5 (m, 2H), 1.65 (m, 4H).

LCMS (Method D): r/t 12.43 (M+H) 370.

Example 26

2-Benzenesulphonylamino-5-(furan-3-yl)-4-methylthiophene-3-carboxylic acid

Prepared by proceeding in a similar manner to Example 20, starting from ethyl 2-benzenesulphonylamino-5-(furan-3-yl)-4-methylthiophene-3-carboxylate (Intermediate 33)

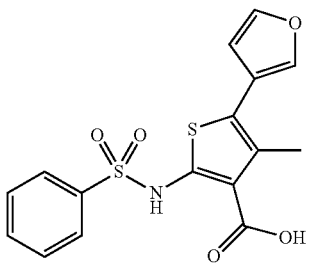 [SMILES: Cc1c(-c2ccoc2)sc(NS(=O)(=O)c2ccccc2)c1C(=O)O]

NMR (DMSO-d$_6$) δ 11.6 (br s, 1H), 7.9 (m, 1H), 7.85 (m, 1H), 7.8 (m, 1H), 7.75 (t, 1H), 7.65 (tt, 1H), 7.55 (m, 2H), 6.65 (dd, 1H), 2.25 (s, 3H).
LCMS (Method D): r/t 11.20 (M+H) 364.

Example 27

2-(2-Ethylbenzenesulphonylamino)-4,5,6,7-tetrahydrobenzo[b]thiophene-3-carboxylic acid Prepared by proceeding in a similar manner to Example 2, starting from ethyl 2-(2-ethylbenzenesulphonylamino)-4,5,6,7-tetrahydrobenzo[b]thiophene-3-carboxylate (Intermediate 36)

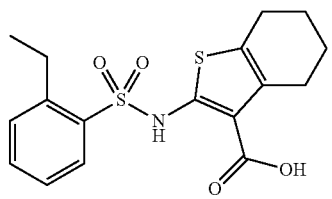 [SMILES: CCc1ccccc1S(=O)(=O)Nc1sc2c(c1C(=O)O)CCCC2]

NMR (DMSO-d$_6$) δ 11.35 (br s, 1H), 7.85 (dd, 1H), 7.6 (dt, 1H), 7.45 (d, 1H), 7.4 (dt, 1H), 3.0 (q, 2H), 2.6 (m, 2H), 2.5 (m, 2H), 1.65 (m, 4H), 1.2 (t, 3H).
LCMS (Method D): r/t 12.46 (M+H) 366.

Example 28

2-[2-((Z)-3-Diethylaminoprop-1-enyl)benzenesulphonylamino]-4,5,6,7-tetrahydrobenzo[b]thiophene-3-carboxylic acid Prepared by proceeding in a similar manner to Example 2, starting from ethyl 2-[2-((1Z)-3-diethylaminoprop-1-en-1-yl)benzenesulphonylamino]-4,5,6,7-tetrahydrobenzo[b]thiophene-3-carboxylate (Intermediate 40 M1, 0.083 g)

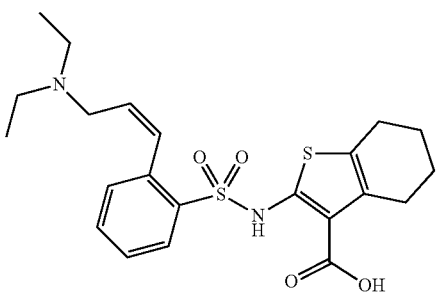 [SMILES: CCN(CC)C/C=C\c1ccccc1S(=O)(=O)Nc1sc2c(c1C(=O)O)CCCC2]

NMR (DMSO-d$_6$): δ 14.2 (br s, 1H), 8.0 (m, 1H), 7.5-7.4 (m, 3H), 7.25 (m, 1H), 5.8 (m, 1H), 3.75 (br s, 2H), 2.9 (br s, 4H), 2.6 (m, 2H), 2.4 (m, 2H), 1.6 (m, 4H), 0.95 (t, 6H).
LCMS (Method C): r/t 3.87 (M+H) 449.

Example 29

2-Benzenesulphonylamino-5,6-dihydro-4H-cyclopenta[b]thiophene-3-carboxylic acid

Prepared by proceeding in a similar manner to Example 2, starting from ethyl 2-benzenesulphonylamino-5,6-dihydro-4H-cyclopenta[b]thiophene-3-carboxylate (Intermediate 43)

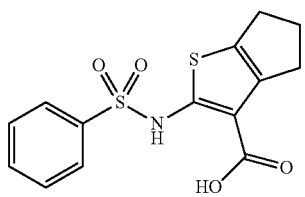 [SMILES: O=C(O)c1c(NS(=O)(=O)c2ccccc2)sc2c1CCC2]

NMR (DMSO-d$_6$) δ 10.6 (br s, 1H), 7.8 (d, 2H), 7.65 (t, 1H), 7.6 (t, 2H), 2.75 (m, 4H), 2.25 (m, 2H)
LCMS (Method C): r/t 4.68 (M+H) 324

Example 30

2-(4-Chlorobenzenesulphonylamino)-4,5,6,7-tetrahydrobenzo[b]thiophene-3-carboxylic acid Prepared by proceeding in a similar manner to Example 2, starting from methyl 2-(4-chlorobenzenesulphonylamino)-4,5,6,7-tetrahydrobenzo[b]thiophene-3-carboxylate (Intermediate 44)

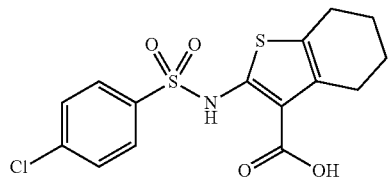 [SMILES: O=C(O)c1c(NS(=O)(=O)c2ccc(Cl)cc2)sc2c1CCCC2]

NMR (DMSO-d$_6$) δ 11.05 (br s, 1H), 7.8 (m, 2H), 7.65 (m, 2H), 2.5 (m, 4H), 1.65 (m, 4H).
LCMS (Method C): r/t 5.38 (M+H) 372/374.

Example 31

2-(3-Chlorobenzenesulphonylamino)-4,5,6,7-tetrahydrobenzo[[b]thiophene-3-carboxylic acid Prepared by proceeding in a similar manner to Example 2, starting from methyl 2-(3-chlorobenzenesulphonylamino)-4,5,6,7-tetrahydrobenzo[b]thiophene-3-carboxylate (Intermediate 45)

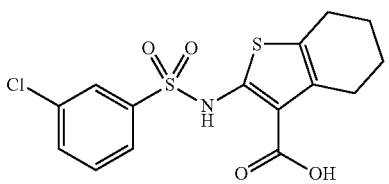 [SMILES: O=C(O)c1c(NS(=O)(=O)c2cccc(Cl)c2)sc2c1CCCC2]

NMR (DMSO-d$_6$) δ 11.15 (br s, 1H), 7.8 (m, 1H), 7.75 (m, 2H), 7.65 (m, 1H), 2.6 (m, 4H), 1.7 (m, 4H).
LCMS (Method C): r/t 5.36 (M+H) 372/374.

Intermediate 1

Ethyl 2-benzenesulphonylamino-4,5,6,7-tetrahydrobenzo[b]thiophene-3-carboxylate

Ethyl 2-amino-4,5,6,7-tetrahydrobenzo[b]thiophene-3-carboxylate (0.113 g) was added to a solution of benzenesulphonyl chloride (0.097 g) in pyridine (5 ml) and the resultant solution was stirred at room temperature for 16 hours. The mixture was diluted with water and extracted with ethyl acetate. The organic phase was washed with hydrochloric acid (1M), water, dried (MgSO$_4$) and filtered. The filtrate was evaporated to dryness and the residue was purified by chromatography on silica, eluting with a mixture of ethyl acetate and pentane (5%) to give ethyl 2-benzenesulphonylamino-4,5,6,7-tetrahydrobenzo[b]thiophene-3-carboxylate (0.076 g) as a pale yellow solid.
NMR (CDCl$_3$) δ 10.45 (br s, 1H), 7.9 (d, 2H), 7.55 (m, 1H), 7.45 (t, 2H), 4.25 (q, 2H), 2.65 (m, 2H), 2.6 (m, 2H), 1.7 (m, 4H), 1.3 (t, 3H).

Intermediate 2

Ethyl 2-(4-fluorobenzenesulphonylamino)-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxylate and 4-fluorobenzene-sulphonyl chloride

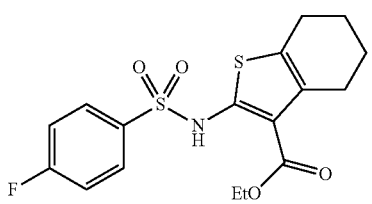

NMR (CDCl$_3$) δ 10.45 (br s, 1H), 7.9 (m, 2H), 7.15 (t, 2H), 4.25 (q, 2H), 2.7 (m, 1H), 2.65 (m, 1H), 2.6 (m, 1H), 2.5 (m, 1H), 1.75 (m, 4H), 1.35 (t, 3H).

Intermediate 3

Ethyl 2-benzenesulphonylaminobenzo[b]thiophene-3-carboxylate

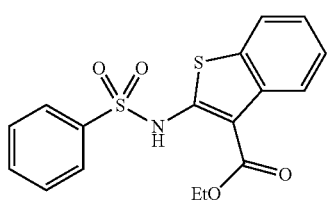 [SMILES: CCOC(=O)c1c(NS(=O)(=O)c2ccccc2)sc2ccccc12]

A mixture of ethyl 2-[bis-(benzenesulphonyl)amino]benzo[b]thiophene-3-carboxylate (Intermediate 4, 0.173 g) and lithium hydroxide mono hydrate (0.043 g) in dioxane (6 ml) and water (3 ml) was stirred and heated at 60° C. for 2.5 hours. After cooling, the mixture was diluted with water and acidified by addition of hydrochloric acid (1M). It was extracted with ethyl acetate, washed with water, dried (MgSO$_4$) and filtered. The filtrate was evaporated to dryness and the residue was purified by chromatography on silica, eluting with a mixture of ethyl acetate and pentane (5-10%) to give ethyl 2-benzenesulphonylaminobenzo[b]thiophene-3-carboxylate (0.075 g) as a white solid.
NMR (CDCl$_3$) δ 11.0 (br s, 1H), 8.15 (d, 1H), 8.0 (d, 2H), 7.65 (d, 1H), 7.55 (t, 1H), 7.5 (t, 2H), 7.4 (t, 1H), 7.3 (d, 1H), 4.45 (q, 2H), 1.45 (t, 3H)

Intermediate 4

Ethyl 2-[bis-(benzenesulphonyl)amino]benzo[b]thiophene-3-carboxylate

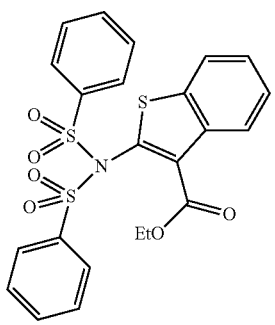 [SMILES: CCOC(=O)c1c(N(S(=O)(=O)c2ccccc2)S(=O)(=O)c2ccccc2)sc2ccccc12]

A mixture of ethyl 2-aminobenzo(b)thiophene-3-carboxylate (0.165 g) and benzenesulphonyl chloride (0.53 g) in pyridine (7 ml) was stirred and heated at 80° C. for 5 hours. Further benzenesulphonyl chloride (0.53 g) was added and the mixture was stirred and heated at 80° C. for 24 hours. The mixture was concentrated and the residue was partitioned between ethyl acetate and water. The aqueous layer was further extracted with ethyl acetate and the combined organic layers were washed with water, dried (MgSO$_4$) and filtered. The filtrate was evaporated to dryness and the residue was purified by chromatography on silica eluting with a mixture of ethyl acetate and pentane (5-10%) to give ethyl 2-[bis-(benzenesulphonyl)amino]benzo[b]thiophene-3-carboxylate (0.173 g) as a colourless oil.

NMR (CDCl₃) δ 8.5 (m, 1H), 8.05 (d, 4H), 7.8 (m, 1H), 7.7 (t, 2H), 7.6 (t, 4H), 7.5 (m, 2H), 3.8 (q, 2H), 1.15 (t, 3H)

Intermediate 5

Methyl 2-benzenesulphonylamino-5-ethyl-4-methylthiophene-3-carboxylate

Prepared by proceeding in a similar manner to Intermediate 1, starting from methyl 2-amino-5-ethyl-4-methylthiophene-3-carboxylate and benzenesulphonyl chloride.

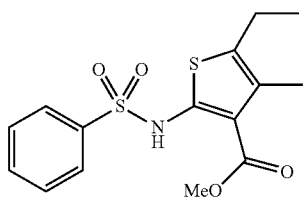 [SMILES: CCc1sc(NS(=O)(=O)c2ccccc2)c(C(=O)OC)c1C]

NMR (CDCl₃) δ 10.3 (br s, 1H), 7.9 (d, 2H), 7.55 (m, 1H), 7.45 (t, 2H), 3.8 (s, 3H), 2.6 (q, 2H), 2.25 (s, 3H), 0.95 (t, 3H).

Intermediate 6

Ethyl 2-benzenesulphonylamino-4,7-dihydro-5H-thieno[2,3-c]pyran-3-carboxylate

Prepared by proceeding in a similar manner to Intermediate 1, starting from ethyl 2-amino-4,7-dihydro-5H-thieno[2,3-c]pyran-3-carboxylate (Intermediate 7) and benzenesulphonyl chloride

NMR (DMSO-d6) δ 10.45 (br s, 1H), 7.8-7.5 (m, 5H), 4.55 (s, 2H), 4.05 (q, 2H), 3.75 (t, 2H), 2.6 (t, 2H), 1.15 (t, 3H).

Intermediate 7

Ethyl 2-amino-4,7-dihydro-5H-thieno[2,3-c]pyran-3-carboxylate

Ethyl cyanoacetate (2.48 g) was added to a suspension of tetrahydropyran-4-one (2.14 g) and sulphur (0.76 g) in IMS (30 ml). The resultant mixture was stirred and heated to 50° C. Morpholine (5.2 ml) was added and the mixture was stirred at 50° C. for a further 2 hours and then allowed to stand at room temperature overnight. The solid was collected by filtration and washed with cold IMS and then dried under vacuum to give ethyl 2-amino-4,7-dihydro-5H-thieno[2,3-c]pyran-3-carboxylate (1.76 g) as a white solid.

NMR (DMSO-d₆) δ 7.2 (br s, 2H), 4.4 (t, 2H), 4.1 (q, 2H), 3.75 (t, 2H), 2.6 (m, 2H), 1.2 (t, 3H).

Intermediate 8

Ethyl 2-benzenesulphonylamino-5-phenylthiophene-3-carboxylate

Prepared by proceeding in a similar manner to Intermediate 1, starting from ethyl 2-amino-5-phenylthiophene-3-carboxylate and benzenesulphonyl chloride

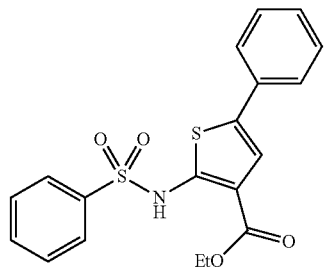 [SMILES: CCOC(=O)c1cc(-c2ccccc2)sc1NS(=O)(=O)c1ccccc1]

LCMS (Method E): r/t 4.85 (M+H) 388

Intermediate 9

Methyl 2-benzenesulphonylamino-4-methyl-5-phenylthiophene-3-carboxylate

Prepared by proceeding in a similar manner to Intermediate 1, starting from methyl 2-amino-4-methyl-5-phenylthiophene-3-carboxylate and benzenesulphonyl chloride

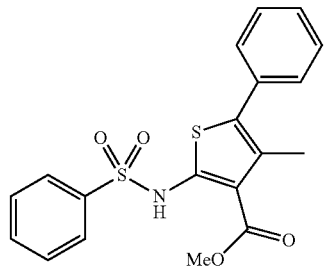 [SMILES: COC(=O)c1c(NS(=O)(=O)c2ccccc2)sc(-c2ccccc2)c1C]

NMR (CDCl₃) δ 10.6 (br s, 1H), 7.95 (d, 2H), 7.6 (t, 1H), 7.5 (t, 2H), 7.4 (d, 2H), 7.35 (m, 3H), 3.85 (s, 3H), 2.45 (s, 3H)

Intermediate 10

Ethyl 2-phenylmethanesulphonylamino-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxlyate and phenylmethanesulphonyl chloride.

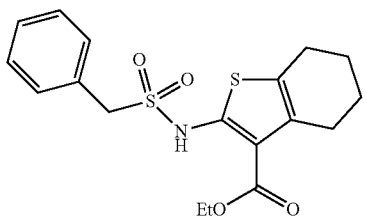 [SMILES: CCOC(=O)c1c(NS(=O)(=O)Cc2ccccc2)sc2c1CCCC2]

NMR (CDCl$_3$) δ 10.0 (br s, 1H), 7.4-7.25 (m, 5H), 4.4 (s, 2H), 4.25 (q, 2H), 2.75 (m, 2H), 2.6 (m, 2H), 1.8 (m, 4H), 1.3 (t, 3H).

LCMS (Method F): r/t 4.79 (M+Na) 402.

Intermediate 11

Ethyl 2-(2-chlorobenzenesulphonylamino)-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxylate and 2-chlorobenzene-sulphonyl chloride

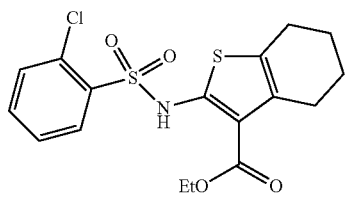 [SMILES: CCOC(=O)c1c(NS(=O)(=O)c2ccccc2Cl)sc2c1CCCC2]

NMR (CDCl$_3$) δ 11.05 (br s, 1H), 8.2 (m, 1H), 7.5 (m, 2H), 7.4 (m, 1H), 4.3 (q, 2H), 2.65 (m, 2H), 2.55 (m, 2H), 1.7 (m, 4H), 1.35 (t, 3H).

LCMS (Method F): r/t 4.90 (M+Na) 422.

Intermediate 12

Ethyl 5,5-dimethyl-2-benzenesulphonylamino-4,5,6,7-tetrahydrobenzo[b]thiophene-3-carboxylate Prepared by proceeding in a similar manner to Intermediate 1, starting from ethyl 2-amino-5,5-dimethyl-4,5,6,7-tetrahydrobenzo[b]thiophene-3-carboxylate (prepared according to Pinkerton et al., *Bioorg. Med. Chem. Lett.*, 2007, 17, 3562-3569) and benzenesulphonyl chloride.

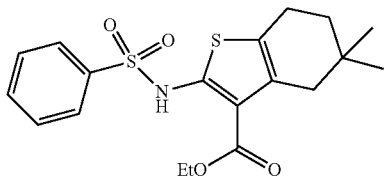 [SMILES: CCOC(=O)c1c(NS(=O)(=O)c2ccccc2)sc2c1CC(C)(C)CC2]

NMR (CDCl$_3$) δ 10.45 (br s, 1H), 7.9 (m, 2H), 7.55 (m, 1H), 7.5 (m, 2H), 4.25 (q, 2H), 2.6 (m, 2H), 2.4 (m, 2H), 1.5 (t, 2H), 1.3 (t, 3H), 0.95 (s, 6H).

LCMS (Method F): r/t 4.91 (M–H) 392.

Intermediate 13

Ethyl 2-(2-methylbenzenesulphonylamino)-4,5,6,7-tetrahydrobenzo[b]thiophen-3-carboxylate Prepared by proceeding in a similar manner to Intermediate 1, starting from ethyl 2-amino-4,5,6,7-tetrahydrobenzo[b]thiophene-3-carboxylate and 2-methylbenzene-sulphonyl chloride.

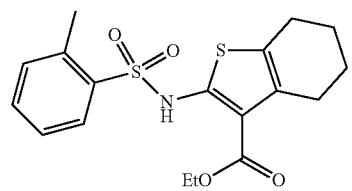 [SMILES: CCOC(=O)c1c(NS(=O)(=O)c2ccccc2C)sc2c1CCCC2]

NMR (CDCl$_3$) δ 10.75 (br s, 1H), 8.05 (dd, 1H), 7.45 (dt, 1H), 7.3 (m, 2H), 4.3 (q, 2H), 2.7 (m, 2H), 2.65 (s, 3H), 2.55 (m, 2H), 1.7 (m, 4H), 1.35 (t, 3H).

LCMS (Method F): r/t 4.99 (M–H) 378.

Intermediate 14

2:1 Mixture of methyl 2-benzenesulphonylamino-6,7-dihydro-4H-thieno[3,2-c]pyran-3-carboxylate and methyl 2-[bis-(benzenesulphonyl)amino]-6,7-dihydro-4H-thieno[3,2-c]pyran-3-carboxylate Prepared by proceeding in a similar manner to Intermediate 1, starting from methyl 2-amino-6,7-dihydro-4H-thieno[3,2-c]pyran-3-carboxylate (Intermediate 16) and benzenesulphonyl chloride

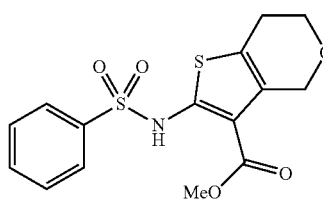

A and

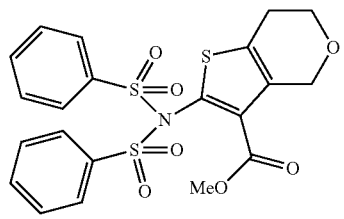

B

NMR (CDCl$_3$) A: δ 10.3 (s, 1H), 7.7 (t, 1H), 7.6 (d, 2H), 7.5 (t, 2H), 4.65 (s, 2H), 3.9 (t, 2H), 3.75 (s, 3H), 2.7 (t, 2H)

B: δ 8.0 (d, 4H), 7.9 (d, 4H), 7.6 (t, 2H), 4.85 (s, 2H), 4.0 (t, 2H), 3.2 (s, 3H), 2.9 (t, 2H) Ratio of A:B by NMR ~2:1

Intermediate 15

Methyl 2-benzenesulphonylamino-3,4-dihydro-2H-thieno[2,3-b]pyran-5-carboxylate

Prepared by proceeding in a similar manner to Intermediate 1 starting from methyl 2-amino-3,4-dihydro-2H-thieno[2,3-b]pyran-5-carboxylate (Intermediate 17)

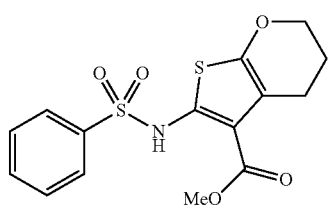 [SMILES: COC(=O)c1c(NS(=O)(=O)c2ccccc2)sc2c1CCCO2]

NMR (CDCl₃) δ 10.0 (br s, 1H), 7.9 (d, 2H), 7.55 (t, 1H), 7.45 (t, 2H), 4.15 (m, 2H), 3.75 (s, 3H), 2.6 (t, 2H), 1.95 (m, 2H)

Intermediates 16 and 17

Methyl 2-amino-6,7-dihydro-4H-thieno[3,2-c]pyran-3-carboxylate (Intermediate 16) and methyl 2-amino-3,4-dihydro-2H-thieno[2,3-b]pyran-5-carboxylate (Intermediate 17)

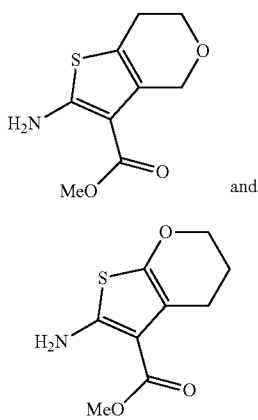

Sulphur (0.352 g) was added to a stirred mixture of dihydropyran-3-one (1.0 g) and methyl cyanoacetate (1.09 g) in methanol (15 ml). Morpholine (1.4 ml) was then added and the resultant mixture was stirred and heated at 55° C. for 4 hours. The mixture was cooled to room temperature and the solid was collected by filtration. The solid was dissolved in ethyl acetate and washed with water, dried (MgSO₄) and filtered. The filtrate was evaporated to dryness to give methyl 2-amino-3,4-dihydro-2H-thieno[2,3-b]pyran-5-carboxylate (Intermediate 17) (1.2 g) as an off white solid.

NMR (CDCl₃) δ 6.0-5.0 (br s, 2H), 4.15 (m, 2H), 3.75 (s, 3H), 2.65 (t, 2H), 2.0 (m, 2H)

The methanol filtrate was evaporated to dryness and the residue was partitioned between ethyl acetate and water. The aqueous layer was extracted with ethyl acetate and the combined organic layers were washed with water, dried (MgSO₄) and filtered. The filtrate was evaporated to dryness and the residue was purified by chromatography on slica, eluting with a mixture of ethyl acetate and pentane (2.5-25%) to give two components. The first was a further 0.145 g of methyl 2-amino-3,4-dihydro-2H-thieno[2,3-b]pyran-5-carboxylate. The second component was methyl 2-amino-6,7-dihydro-4H-thieno[3,2-c]pyran-3-carboxylate (Intermediate 16) (0.09 g) as a white solid.

NMR (CDCl₃) 6.1-5.9 (br s, 2H), 4.7 (s, 2H), 3.9 (t, 2H), 3.75 (s, 3H), 2.6 (m, 2H)

Intermediate 18

Ethyl 5-methyl-2-benzenesulphonylamino-4,5,6,7-tetrahydrobenzo[b]thiophene-3-carboxylate Prepared by proceeding in a similar manner to Intermediate 1, starting from ethyl 2-amino-5-methyl-4,5,6,7-tetrahydrobenzo[b]thiophene-3-carboxylate (prepared according to Pinkerton et al., *Bioorg. Med. Chem. Lett.*, 2007, 17, 3562-3569) and benzenesulphonyl chloride.

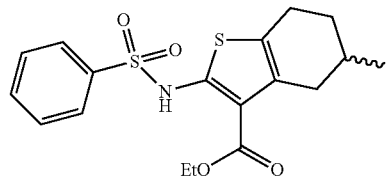 [SMILES: CCOC(=O)c1c(NS(=O)(=O)c2ccccc2)sc2c1CC(C)CC2]

NMR (CDCl₃) δ 10.4 (br s, 1H), 7.9 (m, 2H), 7.55 (m, 1H), 7.5 (m, 2H), 4.25 (q, 2H), 2.85 (dd, 1H), 2.6 (m, 2H), 2.15 (m, 1H), 1.85 (m, 1H), 1.75 (m, 1H), 1.35 (m, 1H), 1.3 (t, 3H), 1.05 (d, 3H).

LCMS (Method F): r/t 4.89 (M+Na) 402.

Intermediate 19

Ethyl 6-methyl-2-benzenesulphonylamino-4,5,6,7-tetrahydrobenzo[b]thiophene-3-carboxylate Prepared by proceeding in a similar manner to Intermediate 1, starting from ethyl 2-amino-6-methyl-4,5,6,7-tetrahydrobenzo[b]thiophene-3-carboxylate (prepared according to Pinkerton et al., *Bioorg. Med. Chem. Lett.*, 2007, 17, 3562-3569) and benzenesulphonyl chloride.

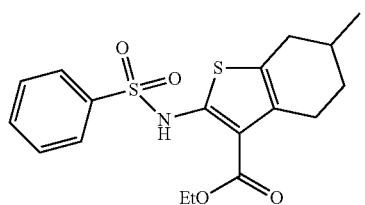 [SMILES: CCOC(=O)c1c(NS(=O)(=O)c2ccccc2)sc2c1CCC(C)C2]

NMR (CDCl₃) δ 10.45 (br s, 1H), 7.9 (m, 2H), 7.6 (m, 1H), 7.5 (m, 2H), 4.25 (q, 2H), 2.8 (m, 1H), 2.65 (m, 1H), 2.55 (m, 1H), 2.2 (m, 1H), 1.85 (m, 2H), 1.35 (t, 3H), 1.3 (m, 1H), 1.05 (d, 3H).

LCMS (Method F): r/t 4.92 (M+Na) 402.

Intermediate 20

Ethyl 6,6-dimethyl-2-benzenesulphonylamino-4,5,6,7-tetrahydrobenzo[b]thiophene-3-carboxylate Prepared by proceeding in a similar manner to Intermediate 1, starting from ethyl 2-amino-6,6-dimethyl-4,5,6,7-tetrahydrobenzo[b]thiophene-3-carboxylate (prepared according to. Pinkerton et al., *Bioorg. Med. Chem. Lett.*, 2007, 17, 3562-3569) and benzenesulphonyl chloride.

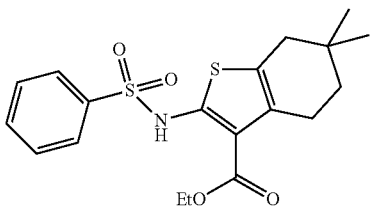 [SMILES: CCOC(=O)c1c(NS(=O)(=O)c2ccccc2)sc2c1CCC(C)(C)C2]

NMR (CDCl₃) δ 10.45 (br s, 1H), 8.4 (m, 2H), 7.55 (m, 1H), 7.5 (m, 2H), 4.25 (q, 2H), 2.65 (t, 2H), 2.35 (m, 2H), 1.45 (t, 2H), 1.3 (t, 3H), 1.0 (s, 6H).

LCMS (Method F): r/t 4.93 (M+Na) 416.

Intermediate 21

Tert-Butyl benzenesulphonylamino-1-methyl-4,5,6,7-tetrahydro-1H-indole-3-carboxylate

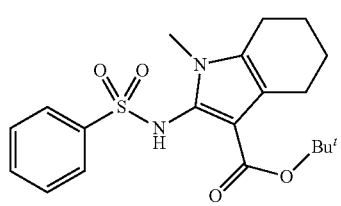

A mixture of tert-butyl cyanoacetate (3.0 ml), 2-chlorocyclohexanone (4.18 g) and methylamine (40% aqueous solution, 16.3 ml) in DCM (25 ml) was stirred and heated at 90° C. with distillation until the volatiles had been removed. The residue was diluted with toluene (100 ml) and the solution was washed with water (3×20 ml) and brine (20 ml), dried (MgSO₄) and filtered. The filtrate was evaporated to dryness and the residue was dissolved in pyridine (70 ml). The solution was cooled to 0° C. and benzenesulphonyl chloride (4.0 ml) was added drop-wise. The cold bath was removed and the mixture was stirred at room temperature for 2 hours. The solvent was removed and the residue was purified directly by chromatography on silica, eluting with a mixture of ethyl acetate and cyclohexane (0-10%) to give tert-butyl 2-benzenesulphonylamino-1-methyl-4,5,6,7-tetrahydro-1H-indole-3-carboxylate (2.63 g) as a white solid.

NMR (CDCl₃) δ 8.2 (br s, 1H), 7.7 (m, 2H), 7.5 (dt, 1H), 7.45 (dt, 2H), 3.35 (s, 3H), 2.6 (t, 2H), 2.5 (t, 2H), 1.75 (m, 4H), 1.25 (s, 9H).

LCMS (Method E): r/t 4.63 (M+Na) 413.

Intermediate 22

Ethyl 2-benzenesulphonylamino-5-(tetrahydropyran-4-yl)thiophene-3-carboxylate

Prepared by proceeding in a similar manner to Intermediate 1, starting from ethyl 2-amino-5-(tetrahydropyran-4-yl)thiophene-3-carboxylate (Intermediate 23) and benzenesulphonyl chloride.

LCMS (Method E): r/t 4.33 (M+Na) 418

Intermediate 23

Ethyl 2-amino-5-(tetrahydropyran-4-yl)thiophene-3-carboxylate

Prepared by proceeding in a similar manner to Intermediate 7, starting from (tetrahydropyran-4-yl)acetaldehyde, sulphur and ethyl cyanoacetate

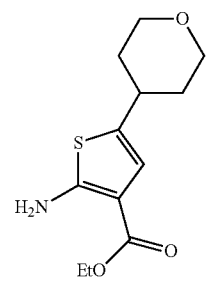 [SMILES: CCOC(=O)c1cc(C2CCOCC2)sc1N]

NMR (DMSO-d6) δ 7.05 (s, 2H), 6.5 (s, 1H), 4.15 (q, 2H), 3.85 (m, 2H), 3.4 (m, 2H), 2.75 (m, 1H), 1.75-1.65 (m, 2H), 1.5-1.4 (m, 2H), 1.2 (t, 3H).

Intermediate 24

Methyl 2-benzenesulphonylamino-5-ethyl-4-isopropylthiophene-3-carboxylate

Prepared by proceeding in a similar manner to Intermediate 1, starting from methyl 2-amino-5-ethyl-4-isopropylthiophene-3-carboxylate (Intermediate 25) and benzenesulphonyl chloride

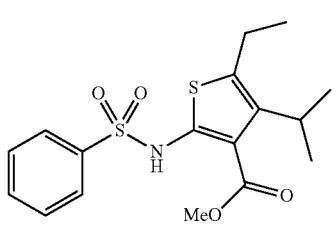 [SMILES: CCc1sc(NS(=O)(=O)c2ccccc2)c(C(=O)OC)c1C(C)C]

NMR (CDCl$_3$) δ 9.9 (br s, 1H), 7.85 (d, 2H), 7.55 (t, 1H), 7.45 (t, 2H), 3.75 (s, 3H), 3.4 (m, 1H), 2.75 (q, 2H), 1.25 (t, 3H), 1.2 (d, 6H)

Intermediate 25

Methyl 2-amino-5-ethyl-4-isopropylthiophene-3-carboxylate

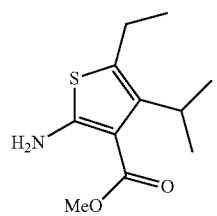

A mixture of methyl 2-cyano-3-propyl-4-methylpent-2-enoate (mixture of E and Z isomers, Intermediate 26, 0.975 g), sulphur (0.18 g) and diethylamine (0.57 ml) in methanol (5 ml) was stirred and heated at 60° C. for 7 hours. The mixture was poured into water and extracted with ethyl acetate, washed with water, dried (MgSO$_4$) and filtered. The filtrate was evaporated to dryness and the residue was purified by chromatography on silica, eluting with a mixture of ethyl acetate and pentane (1-3%) to give methyl 2-amino-5-ethyl-4-isopropylthiophene-3-carboxylate (0.265 g) as a colourless oil.

NMR (CDCl$_3$) δ 3.8 (s, 3H), 3.55 (m, 1H), 2.65 (q, 2H), 1.25 (d, 6H), 1.15 (t, 3H)

Intermediate 26

Methyl 2-cyano-3-propyl-4-methylpent-2-enoate (mixture of E and Z isomers)

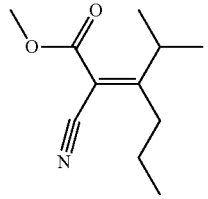

A mixture of methyl cyanoacetate (1.98 g), 2-methylhexan-3-one (3.76 g), ammonium acetate (0.196 g) and glacial acetic acid (0.288 ml) in toluene (10 ml) was stirred and heated at reflux with removal of water using a Dean and Stark apparatus for 6 hours. After cooling to room temperature the mixture was diluted with ethyl acetate and washed with water, dried (MgSO$_4$) and filtered. The filtrate was evaporated to dryness and the residue was purified by chromatography on silica eluting with a mixture of ethyl acetate and pentane (2%) to give methyl 2-cyano-3-propyl-4-methylpent-2-enoate (as a mixture of E and Z isomers) (2.11 g) as a colourless oil.

NMR (CDCl$_3$) δ 4.1 (m, 0.4H), 3.85 (s, 3H), 3.3 (m, 0.6H), 2.55 (m, 1.2H), 2.45 (m, 0.8H), 1.65 (m, 0.8H), 1.5 (m, 1.2H), 1.15 (d, 3.6H), 1.1 (d, 2.4H), 1.05 (2t, 3H)

Intermediate 27

Ethyl 2-(2-trifluoromethylbenzenesulphonylamino)-4,5,6,7-tetrahydrobenzo[b]-thiophene-3-carboxylate

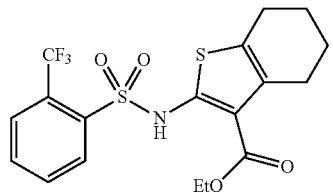 [SMILES: CCOC(=O)c1c(NS(=O)(=O)c2ccccc2C(F)(F)F)sc2c1CCCC2]

2-Trifluoromethylbenzenesulphonyl chloride (0.195 g) was added to a solution of ethyl 2-amino-4,5,6,7-tetrahydrobenzo[b]thiophene-3-carboxylate (0.150 g) in pyridine (1.7 ml) at room temperature and the resultant mixture was stirred for 64 hours. The solvent was removed and the residue was purified directly by chromatography on silica, eluting with a mixture of ethyl acetate and cyclohexane (0-20%) to give ethyl 2-(2-trifluoromethylbenzenesulphonylamino)-4,5,6,7-tetrahydrobenzo[b]thiophene-3-carboxylate (0.194 g) as a white solid.

NMR (CDCl$_3$) δ 10.85 (br s, 1H), 8.3 (dd, 1H), 7.85 (dd, 1H), 7.7 (dt, 2H), 4.3 (q, 2H), 2.65 (t, 2H), 2.55 (t, 2H), 1.75 (m, 4H), 1.35 (t, 3H).

LCMS (Method E): r/t 4.87 (M+Na) 456.

Intermediate 28

Ethyl 2-(2-fluorobenzenensulphonylamino)-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxlyate and 2-fluorobenzene-sulphonyl chloride.

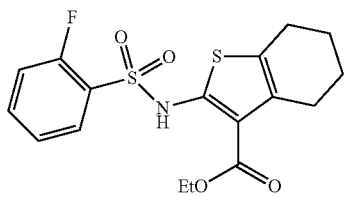 [SMILES: CCOC(=O)c1c(NS(=O)(=O)c2ccccc2F)sc2c1CCCC2]

NMR (CDCl$_3$) δ 10.75 (br s, 1H), 7.95 (m, 1H), 7.55 (m, 1H), 7.25 (m, 1H), 7.2 (m, 1H), 4.3 (q, 2H), 2.65 (m, 2H), 2.55 (m, 2H), 1.75 (m, 4H), 1.35 (t, 3H).

LCMS (Method F): r/t 4.28 (M−H) 382.

Intermediate 29

Ethyl 2-(cyclohexanesulphonylamino)-4,5,6,7-tetrahydrobenzo[b]thiophene-3-carboxylate Prepared by proceeding in a similar manner to Intermediate 27, starting from ethyl-2-amino-4,5,6,7-tetrahydrobenzo[b]thiophene-3-carboxylate and cyclohexanesulphonyl chloride.

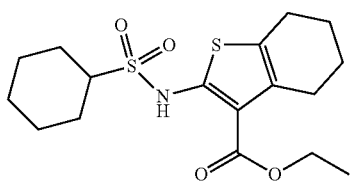 [SMILES: CCOC(=O)c1c(NS(=O)(=O)C2CCCCC2)sc2c1CCCC2]

NMR (CDCl$_3$) δ 10.2 (br s, 1H), 4.35 (q, 2H), 3.1 (m, 1H), 2.75 (m, 2H), 2.6 (m, 2H), 2.3-2.1 (m, 4H), 2.0-1.5 (m, 8H), 1.4 (t, 3H), 1.35-1.1 (m, 2H).
LCMS (Method F): r/t 5.01 (M+Na) 394.

Intermediate 30

Ethyl 2-(2-methoxybenzenesulphonylamino)-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxlyate and 2-methoxybenzene-sulphonyl chloride.

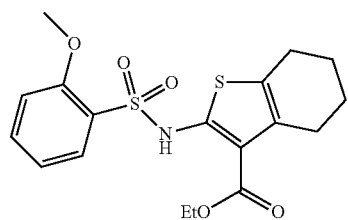 [SMILES: CCOC(=O)c1c(NS(=O)(=O)c2ccccc2OC)sc2c1CCCC2]

NMR (CDCl$_3$) δ 10.95 (br s, 1H), 7.95 (m, 1H), 7.5 (m, 1H), 7.0 (m, 1H), 6.95 (m, 1H), 4.3 (q, 2H), 3.95 (s, 3H), 2.65 (m, 2H), 2.55 (m, 2H), 1.7 (m, 4H), 1.35 (t, 3H).
LCMS (Method F): r/t 4.79 (M+Na) 418.

Intermediate 31

Ethyl 2-(3-methoxybenzenesulphonylamino)-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxlyate and 3-methoxybenzenesulphonyl chloride.

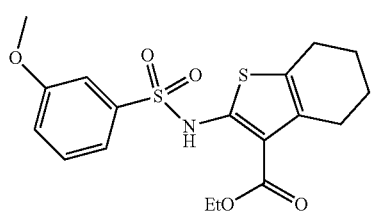 [SMILES: CCOC(=O)c1c(NS(=O)(=O)c2cccc(OC)c2)sc2c1CCCC2]

NMR (CDCl$_3$) δ 10.45 (br s, 1H), 7.5 (m, 1H), 7.45-7.35 (m, 2H), 7.1 (m, 1H), 4.25 (q, 2H), 3.85 (s, 3H), 2.65 (m, 2H), 2.6 (m, 2H), 1.75 (m, 4H), 1.3 (t, 3H).
LCMS (Method F): r/t 4.34 (M+Na) 418.

Intermediate 32

2:1 Mixture of ethyl 2-(4-fluoro-2-methylbenzenesulphonylamino)-4,5,6,7-tetrahydrobenzo[b]thiophene-3-carboxylate and ethyl 2-[bis-(4-fluoro-2-methylbenzenesulphonyl)amino]-4,5,6,7-tetrahydrobenzo[b]thiophene-3-carboxylate Prepared by proceeding in a similar manner to Intermediate 1, starting from ethyl 2-amino-4,5,6,7-tetrahydrobenzo[b]thiophene-3-carboxylate and 4-fluoro-2-methylbenzenesulphonyl chloride

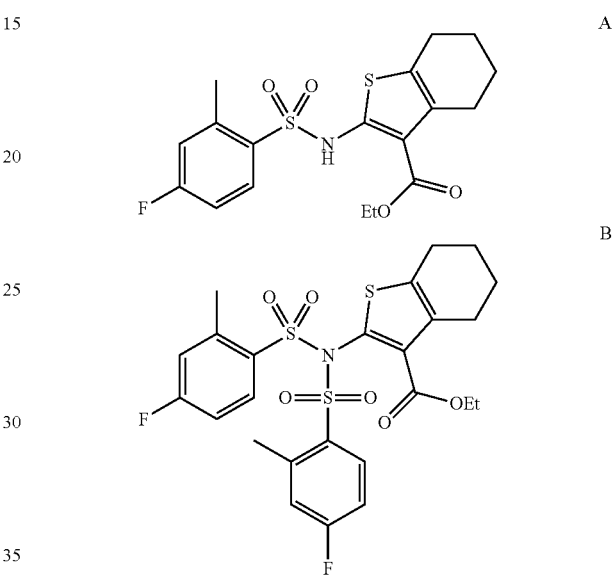

NMR (CDCl$_3$) A: δ 10.75 (br s, 1H), 8.05 (m, 1H), 7.0 (m, 2H), 4.3 (q, 2H), 2.75 (m, 2H), 2.7 (s, 3H), 2.55 (m, 2H), 1.7 (m, 4H), 1.35 (t, 3H).
LCMS (Method E): r/t 4.95 (M+Na) 420.
NMR (CDCl$_3$) B: δ 8.05 (m, 2H), 7.0 (m, 4H), 3.95 (q, 2H), 2.65 (m, 4H), 2.5 (s, 6H), 1.8 (m, 4H), 1.15 (t, 3H).
LCMS (Method E): r/t 4.95 (M+Na) 592.

Intermediate 33

Ethyl 2-benzenesulphonylamino-5-(furan-3-yl)-4-methylthiophene-3-carboxylate

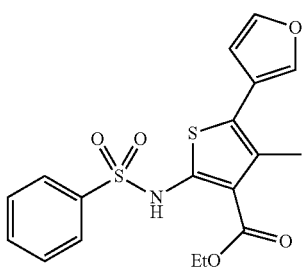 [SMILES: CCOC(=O)c1c(NS(=O)(=O)c2ccccc2)sc(-c2ccoc2)c1C]

A mixture of ethyl 2-benzenesulphonylamino-5-bromo-4-methylthiophene-3-carboxylate (Intermediate 34, 0.134 g), 3-furan boronic acid (0.056 g) and potassium carbonate (0.114 g) in dioxane (1.3 ml) and water (0.33 ml) was degassed and placed under nitrogen. Tetrakis(triphenylphosphine)palladium(0) (0.019 g) was added and the mixture was heated in the microwave at 150° C. for 15 minutes. The solvent was removed and the residue was purified by chromatography on silica, eluting with a mixture of ethyl acetate and cyclohexane (0-20%) to give ethyl 2-benzenesulphonylamino-5-(furan-3-yl)-4-methyl-thiophene-3-carboxylate (0.047 g) as a white solid.

NMR (CDCl₃) δ 10.6 (br s, 1H), 7.95 (m, 2H), 7.55 (m, 1H), 7.5 (m, 4H), 6.5 (m, 1H), 4.3 (q, 2H), 2.3 (s, 3H), 1.35 (t, 3H).

LCMS (Method E) r/t 4.64 (M+Na) 414.

Intermediate 34

Ethyl 2-benzenesulphonylamino-5-bromo-4-methylthiophene-3-carboxylate

Prepared by proceeding in a similar manner to Intermediate 1, starting from ethyl 2-amino-5-bromo-4-methylthiophene-3-carboxylate (Intermediate 35) and benzenesulphonyl chloride

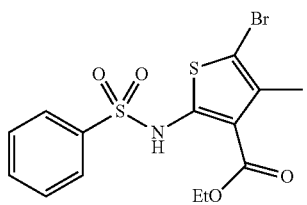 [SMILES: CCOC(=O)c1c(NS(=O)(=O)c2ccccc2)sc(Br)c1C]

LCMS (Method E) r/t 4.79 (M+H) 403/405.

Intermediate 35

Ethyl 2-amino-5-bromo-4-methylthiophene-3-carboxylate

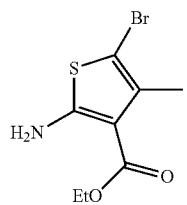

N-Bromosuccinimide (1.78 g) was added portion-wise to a solution of ethyl 2-amino-4-methylthiophene-3-carboxylate (1.71 g) in chloroform (25 ml) at 0° C. After 1 hour, the mixture was diluted with chloroform (20 ml) and washed with a mixture of brine and saturated aqueous sodium hydrogen carbonate (100 ml, 1:1). The organic phase was dried (MgSO₄) and filtered. The filtrate was evaporated to dryness and the residue was purified by chromatography on silica, eluting with a mixture of ethyl acetate and cyclohexane (0-20%) to give ethyl 2-amino-5-bromo-4-methylthiophene-3-carboxylate (1.32 g) as a bright yellow solid.

NMR (CDCl₃) δ 6.05 (br s, 2H), 4.3 (q, 2H), 2.25 (s, 3H), 1.35 (t, 3H).

Intermediate 36

Ethyl 2-(2-ethylbenzenesulphonylamino)-4,5,6,7-tetrahydrobenzo[b]thiophene-3-carboxylate

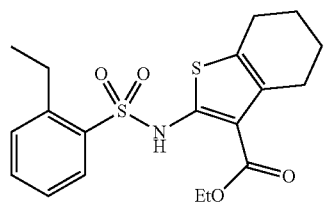 [SMILES: CCOC(=O)c1c(NS(=O)(=O)c2ccccc2CC)sc2c1CCCC2]

A solution of ethyl 2-[N-(2-ethylbenzenesulphonyl)-N-(2-trimethylsilylethoxymethyl)amino]-4,5,6,7-tetrahydrobenzo[b]thiophene-3-carboxylate (Intermediate 37, 0.107 g) in concentrated hydrochloric acid (1 ml) and methanol (3 ml) was heated at 80° C. for 1 hour. After cooling to room temperature, the mixture was added drop-wise to a mixture of ice and saturated aqueous sodium hydrogen carbonate solution (25 ml) and then extracted with ethyl acetate (3×15 ml). The combined organic layers were washed with brine (5 ml), dried (MgSO₄) and filtered. The filtrate was evaporated to dryness and the residue was purified by chromatography on silica, eluting with a mixture of ethyl acetate and cyclohexane (0-20%) to give ethyl 2-(2-ethylbenzenesulphonylamino)-4,5,6,7-tetrahydrobenzo[b]thiophene-3-carboxylate (0.041 g) as a white solid.

NMR (CDCl₃) δ 10.7 (s, 1H), 8.05 (dd, 1H), 7.5 (dt, 1H), 7.35 (m, 1H), 7.3 (dt, 1H), 4.3 (q, 2H), 3.1 (q, 2H), 2.65 (t, 2H), 2.55 (t, 2H), 1.7 (m, 4H), 1.35 (t, 3H), 1.3 (t, 3H).

LCMS (Method E): r/t 4.99 (M+Na) 416.

Intermediate 37

Ethyl 2-[N-(2-ethylbenzenesulphonyl)-N-(2-trimethylsilylethoxymethyl)amino]-4,5,6,7-tetrahydrobenzo[b]thiophene-3-carboxylate

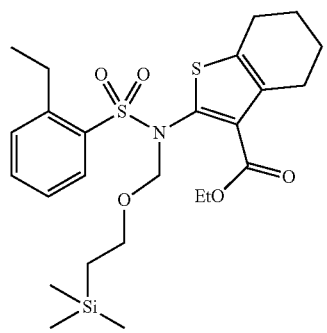 [SMILES: CCOC(=O)c1c(N(COCC[Si](C)(C)C)S(=O)(=O)c2ccccc2CC)sc2c1CCCC2]

Tetrakis(triphenylphosphine)palladium(0) (0.035 g) was added to a degassed solution of ethyl 2-[N-(2-bromobenzenesulphonyl)-N-(2-trimethylsilylethoxymethyl)amino]-4,5,6,7-tetrahydrobenzo[b]thiophene-3-carboxylate (Intermediate 38, 0.344 g), triethylborane (0.90 ml, 1M in THF) and potassium phosphate (0.276 g) in toluene (2.5 ml) and water (0.5 ml). The vessel was sealed and heated at 120° C. for 1 hour. The mixture was cooled, the water removed by separation and the resultant solution was dried (MgSO₄) and filtered. The filtrate was evaporated to dryness and the residue was purified by chromatography on silica, eluting with a mixture of ethyl acetate and cyclohexane (0-10%) to give ethyl 24N-(2-ethylbenzenesulphonyl)-N-(2-trimethylsilylethoxymethyl)amino-1-4,5,6,7-tetrahydrobenzo[b]thiophene-3-carboxylate (0.107 g) as a colourless oil.

NMR (CDCl₃) δ 7.8 (dd, 1H), 7.45 (dt, 1H), 7.25 (m, 2H), 5.25 (s, 2H), 3.95 (q, 2H), 3.65 (m, 2H), 2.85 (q, 2H), 2.7 (t, 2H), 2.6 (t, 2H), 1.75 (m, 4H), 1.25 (t, 3H), 1.2 (t, 3H), 0.95 (m, 2H), 0.0 (s, 9H).

LCMS (Method E): r/t 5.26 (M+Na) 546.

Intermediate 38

Ethyl 2-[N-(2-bromobenzenesulphonyl)-N-(2-trimethylsilylethoxymethyl)amino]-4,5,6,7-tetrahydrobenzo[b]thiophene-3-carboxylate

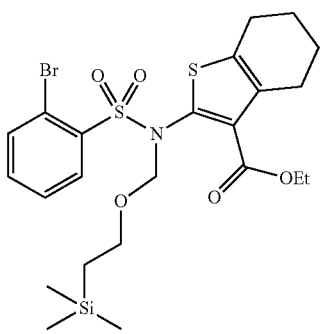 [SMILES: CCOC(=O)c1c(N(COCC[Si](C)(C)C)S(=O)(=O)c2ccccc2Br)sc2c1CCCC2]

Sodium hydride (60% dispersion in oil, 0.081 g) was added to a solution of ethyl 2-(2-bromobenzenesulphonylamino)-4,5,6,7-tetrahydrobenzo[b]thiophene-3-carboxylate (Intermediate 39, 0.700 g) in anhydrous THF at 0° C. under nitrogen. The mixture was allowed to warm to room temperature and then stirred for 15 minutes. The mixture was then cooled to 0° C., 2-trimethysilylethoxymethyl chloride (0.360 ml) was added and the resultant mixture was stirred at room temperature for a further 64 hours. The reaction mixture was quenched by addition of saturated aqueous ammonium chloride (30 ml) and the product was extracted with ethyl acetate. The organic layer was washed with brine, dried (MgSO₄) and filtered. The filtrate was evaporated to dryness and the residue was purified by chromatography on silica, eluting with a mixture of ethyl acetate and cyclohexane (0-20%) to give ethyl 2-[N-(2-bromobenzenesulphonyl)-N-(2-trimethylsilylethoxymethyl)amino]-4,5,6,7-tetrahydrobenzo[b]thiophene-3-carboxylate (0.800 g) as a colourless oil.

NMR (CDCl₃) δ 7.9 (m, 1H), 7.7 (m, 1H), 7.35 (m, 2H), 5.4 (s, 2H), 4.0 (q, 2H), 3.75 (m, 2H), 2.7 (t, 2H), 2.6 (t, 2H), 1.8 (m, 4H), 1.2 (t, 3H), 1.0 (m, 2H), 0.05 (s, 9H).

LCMS (Method E): r/t 5.15 (M+Na) 596/598.

Intermediate 39

Ethyl 2-(2-bromobenzenesulphonylamino)-4,5,6,7-tetrahydrobenzo[b]thiophene-3-carboxylate Prepared by proceeding in a similar manner to Intermediate 27, starting from ethyl 2-amino-4,5,6,7-tetrahydrobenzo[b]thiophene-3-carboxylate (2.00 g) and 2-bromobenzenesulphonyl chloride (4.50 g).

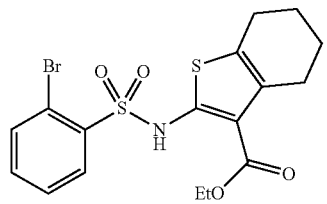 [SMILES: CCOC(=O)c1c(NS(=O)(=O)c2ccccc2Br)sc2c1CCCC2]

NMR (DMSO-d₆) δ 10.95 (br s, 1H), 8.1 (m, 1H), 7.9 (m, 1H), 7.6 (m, 2H), 4.25 (q, 2H), 2.6 (t, 2H), 2.5 (t, 2H), 1.65 (m, 4H), 1.25 (t, 3H).

LCMS (Method E): r/t 4.91 (M+Na) 466/468.

Intermediate 40

Ethyl 2-[2-((Z)-3-diethylaminoprop-1-enyl)benzenesulphonylamino]-4,5,6,7-tetrahydrobenzo[b]thiophene-3-carboxylate Prepared by proceeding in a similar manner to Intermediate 36, starting from ethyl 2-{2-N-[2-((Z)-3-dimethylaminoprop-1-enyl)benzenesulphonyl]-N-(2-trimethylsilylethoxymethyl]amino}-4,5,6,7-tetrahydrobenzo[b]thiophene-3-carboxylate (Intermediate 41)

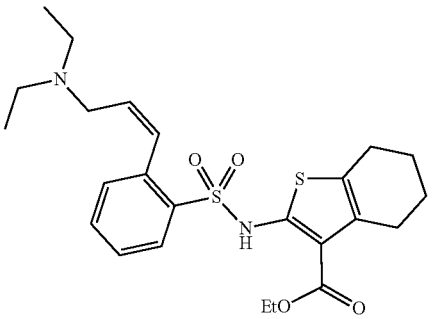 [SMILES: CCOC(=O)c1c(NS(=O)(=O)c2ccccc2/C=C\CN(CC)CC)sc2c1CCCC2]

NMR (CDCl₃) δ 10.75 (br s, 1H), 8.1 (m, 1H), 7.6 (m, 1H), 7.5 (m, 1H), 7.3 (m, 1H), 7.2 (m, 1H), 6.3 (m, 1H), 4.3 (q, 2H), 3.7 (m, 2H), 3.05 (m, 4H), 2.65 (m, 2H), 2.55 (m, 2H), 1.75 (m, 4H), 1.35 (t, 3H), 1.25 (t, 6H).

LCMS (Method F): r/t 3.60 (M+H) 477.

Intermediate 41

Ethyl 2-{2-N-[2-((Z)-3-dimethylaminoprop-1-enyl)benzenesulphonyl]-N-(2-trimethylsilylethoxymethyl]amino}-4,5,6,7-tetrahydrobenzo[b]thiophene-3-carboxylate

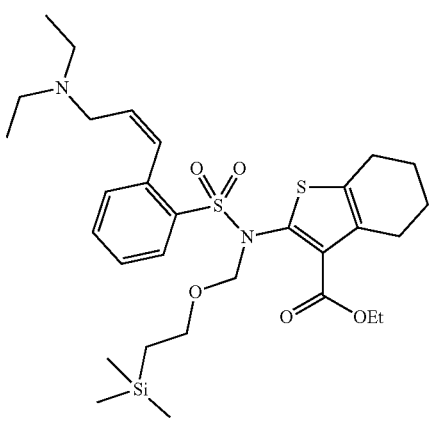 [SMILES: CCOC(=O)c1c(N(COCC[Si](C)(C)C)S(=O)(=O)c2ccccc2/C=C\CN(CC)CC)sc2c1CCCC2]

A stirred mixture of ethyl 2-{2-N-[2-((Z)-3-hydroxyprop-1-enyl)benzenesulphonyl]-N-(2-trimethylsilylethoxymethyl]amino}-4,5,6,7-tetrahydrobenzo[b]thiophene-3-carboxylate (Intermediate 42, 0.397 g) and N,N-diisopropyl-N-ethylamine (0.214 g) in DCM (10 ml) was cooled to 0° C. in a salt/ice bath. Methanesulphonyl chloride (0.14 g) was added and the mixture was stirred at 0° C. for 2 hours. Diethylamine (0.263 g) was then added, and the mixture was allowed to warm to room temperature and stirred for 48 hrs. The resultant mixture was evaporated to dryness and the residue was purified by chromatography on silica, eluting with a mixture of methanol and dichloromethane (0-8%) to give ethyl 2-{2-N-[2-((Z)-3-dimethylaminoprop-1-enyl)benzenesulphonyl]-N-(2-trimethylsilylethoxymethyl]amino}-4,5,6,7-tetrahydrobenzo[b]thiophene-3-carboxylate (0.323 g) as a brown oil.

NMR (CDCl$_3$) δ 7.85 (d, 1H), 7.55 (t, 1H), 7.4 (t, 1H), 7.15 (d, 1H), 7.0 (d, 1H), 6.05 (m, 1H), 5.2 (s, 2H), 3.95 (q, 2H), 3.65 (m, 2H), 3.6 (m, 2H), 2.95 (br s, 4H), 2.65 (m, 2H), 2.6 (m, 2H), 1.75 (m, 4H), 1.2 (t, 3H), 1.15 (t, 6H), 0.95 (m, 2H), 0.0 (s, 9H).

LCMS (Method F): r/t 4.14 (M+H) 607.

Intermediate 42

Ethyl 2-{2-N-[2-((Z)-3-hydroxyprop-1-enyl)benzenesulphonyl]-N-(2-trimethylsilylethoxymethyl]amino}-4,5,6,7-tetrahydrobenzo[b]thiophene-3-carboxylate Bis-(tri-tert-butylphosphine)palladium(0) (0.66 g) was placed in a microwave vial, which was sealed, evacuated and purged with argon. A solution of ethyl 2-[N-(2-bromobenzenesulphonyl)-N-(2-trimethylsilylethoxymethyl)amino]-4,5,6,7-tetrahydrobenzo[b]thiophene-3-carboxylate (Intermediate 38, 0.732 g) in anhydrous toluene (6 ml) was added and the resulting red solution was degassed with argon, and a solution of (2Z)-3-(tributylstannyl)prop-2-en-1-ol (prepared according to Corey et al, *Tetrahedron Letters*, 1984, 25, 2411-2512, 0.53 g) in anhydrous toluene (4 ml) was added and the mixture was heated to 50° C. for 1 hour. After cooling to room temperature, the mixture was loaded directly onto a silica column and purified by chromatography eluting with a mixture of ethyl acetate and cyclohexane (0-40%) to give ethyl 2-{2-N-[2-((Z)-3-hydroxyprop-1-enyl)benzenesulphonyl]-N-(2-trimethylsilylethoxymethyl]amino}-4,5,6,7-tetrahydrobenzo[b]thiophene-3-carboxylate (0.418 g) as a brown oil.

NMR (CDCl$_3$) δ 7.8 (d, 1H), 7.45 (t, 1H), 7.4 (t, 1H), 7.15 (d, 1H), 7.1 (d, 1H), 6.0 (m, 1H), 5.2 (s, 2H), 4.2 (d, 2H), 3.85 (q, 2H), 3.65 (m, 2H), 2.65 (m, 2H), 2.6 (m, 2H), 1.75 (m, 4H), 1.15 (t, 3H), 0.9 (m, 2H), 0.0 (s, 9H).

LCMS (Method F): r/t 5.13 (M+Na) 574.

Intermediate 43

Ethyl 2-benzenesulphonylamino-5,6-dihydro-4H-cyclopenta[b]thiophene-3-carboxylate Prepared by proceeding in a similar manner to Intermediate 1, starting from ethyl 2-amino-5,6-dihydro-4H-cyclopenta[b]thiophene-3-carboxylate and benzenesulphonyl chloride.

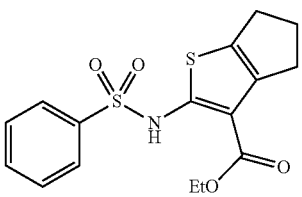 [SMILES: CCOC(=O)c1c(NS(=O)(=O)c2ccccc2)sc2c1CCC2]

LCMS (Method E): r/t 4.63 (M+H) 352

Intermediate 44

Methyl 2-(4-chlorobenzenesulphonylamino)-4,5,6,7-tetrahydrobenzo[b]thiophen-3-carboxylate Prepared by proceeding in a similar manner to Intermediate 1, starting from methyl 2-amino-4,5,6,7-tetrahydrobenzo[b]thiophene-3-carboxylate and 4-chlorobenzene-sulphonyl chloride

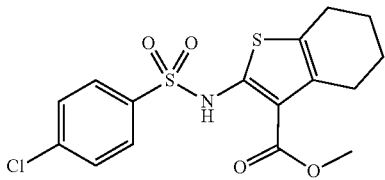 [SMILES: COC(=O)c1c(NS(=O)(=O)c2ccc(Cl)cc2)sc2c1CCCC2]

NMR (CDCl$_3$) δ 10.45 (br s, 1H), 7.85 (m, 2H), 7.45 (m, 2H), 3.8 (s, 3H), 2.65 (m, 2H), 2.6 (m, 2H), 1.75 (m, 4H).
LCMS (Method F): r/t 4.39 (M+Na) 408.

Intermediate 45

Methyl 2-(3-chlorobenzenesulphonylamino)-4,5,6,7-tetrahydrobenzo[b]thiophene-3-carboxylate Prepared by proceeding in a similar manner to Intermediate 1, starting from methyl 2-amino-4,5,6,7-tetrahydrobenzo[b]thiophene-3-carboxylate and 3-chlorobenzene-sulfonyl chloride.

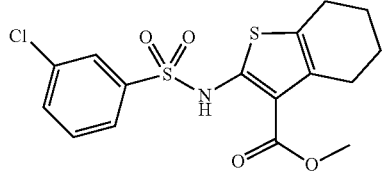 [SMILES: COC(=O)c1c(NS(=O)(=O)c2cccc(Cl)c2)sc2c1CCCC2]

NMR (CDCl$_3$) δ 10.45 (br s, 1H), 7.9 (m, 1H), 7.8 (m, 1H), 7.55 (m, 1H), 7.45 (t, 1H), 3.8 (s, 3H), 2.65 (m, 2H), 2.6 (m, 2H), 1.75 (m, 4H).
LCMS (Method F): r/t 4.86 (M+Na) 408.

Biological Activity

Compounds are tested for their capacity to inhibit recombinant human MetAP2 activity using the following assay.

Human recombinant Flag-MetAP2 expressed in Sf9 cells followed by affinity purification and EDTA treatment to remove endogenous active site cation is dialysed against MnCl$_2$ to produce the manganese enzyme used in the assay. The assay is carried out for 30 minutes at 25° C. in 50 mM HEPES buffer containing 100 mM NaCl, pH 7.5 the presence of 0.75 mM Methionine-Alanine-Serine (MAS) substrate and 50 m/ml amino acid oxidase using a dilution of purified MetAP2 giving approximately 50,000 RFU control activity. Cleavage of the substrate by MetAP2 and oxidation of free methionine by amino acid oxidase is detected and quantified using fluorescence generated by Amplex red (10-acetyl-3,7-dihydroxyphenoxazine) in combination with horseradish peroxidase which detects H$_2$O$_2$ released during the oxidation step. The fluorescent signal is detected using a multiwell fluorimeter. Compounds are diluted in DMSO prior to addition to assay buffer, the final DMSO concentration in the assay being 1%.

The IC$_{50}$ is defined as the concentration at which a given compound achieves 50% inhibition of control. IC$_{50}$ values are calculated using the XLfit software package (version 2.0.5).

Compounds of the invention demonstrated activity in the assay of this Example as indicated in the following table, wherein A represents IC$_{50}$<0.2 μM, B represents IC$_{50}$ between 0.2 μM and 2 μM, and C represents IC$_{50}$>2 μM.

| Compound name | Activity |
| --- | --- |
| 2-Benzenesulphonylamino-4,5,6,7-tetrahydrobenzo[b]thiophene-3-carboxylic acid | A |
| 2-(4-Fluorobenzenesulphonylamino)-4,5,6,7-tetrahydrobenzo[b]thiophene-3-carboxylic acid | A |
| 2-Benzenesulphonylaminobenzo(b)thiophene-3-carboxylic acid | C |
| 2-Benzenesulphonylamino-5-ethyl-4-methylthiophene-3-carboxylic acid | B |
| 2-Benzenesulphonylamino-4,7-dihydro-5H-thieno[2,3-c]pyran-3-carboxylic acid | B |
| 2-Benzenesulphonylamino-5-phenylthiophene-3-carboxylic acid | C |
| 2-Benzenesulphonylamino-4-methyl-5-phenylthiophene-3-carboxylic acid | C |
| 2-Benzylsulphonylamino-4,5,6,7-tetrahydrobenzo[b]thiophene-3-carboxylic acid | B |
| 2-(2-Chlorobenzenesulphonylamino)-4,5,6,7-tetrahydrobenzo[b]thiophene-3-carboxylic acid | B |
| 2-Benzenesulphonylamino-5,5-dimethyl-4,5,6,7-tetrahydrobenzo[b]thiophene-3-carboxylic acid | B |
| 2-(2-Methylbenzenesulphonylamino)-4,5,6,7-tetrahydrobenzo[b]thiophen-3-carboxylic acid | A |
| 2-Benzenesulphonylamino-6,7-dihydro-4H-thieno[3,2-c]pyran-3-carboxylic acid | B |
| 2-Benzenesulphonylamino-3,4-dihydro-2H-thieno[2,3-b]pyran-5-carboxylic acid | A |
| 2-Benzenesulphonylamino-5-methyl-4,5,6,7-tetrahydrobenzo[b]thiophene-3-carboxylic acid | B |
| 2-Benzenesulphonylamino-6-methyl-4,5,6,7-tetrahydrobenzo[b]thiophene-3-carboxylic acid | A |
| 2-Benzenesulphonylamino-6,6-dimethyl-4,5,6,7-tetrahydrobenzo[b]thiophene-3-carboxylic acid | B |
| 2-Benzenesulphonylamino-1-methyl-4,5,6,7-tetrahydro-1H-indole-3-carboxylic acid | B |
| 2-Benzenesulphonylamino-5-(tetrahydropyran-4-yl)thiophene-3-carboxylic acid | C |
| 2-Benzenesulphonylamino-5-ethyl-4-isopropylthiophene-3-carboxylic acid | B |
| 2-(2-Trifluoromethylbenzenesulphonylamino)-4,5,6,7-tetrahydrobenzo[b]thiophene-3-carboxylic acid | B |
| 2-(2-Fluorobenzenesulphonylamino)-4,5,6,7-tetrahydrobenzo[b]thiophene-3-carboxylic acid | B |
| 2-(Cyclohexanesulphonylamino)-4,5,6,7-tetrahydrobenzo[b]thiophene-3-carboxylic acid | B |
| 2-(2-Methoxybenzenesulphonylamino)-4,5,6,7-tetrahydrobenzo[b]thiophene-3-carboxylic acid | A |
| 2-(3-Methoxybenzenensulphonylamino)-4,5,6,7-tetrahydrobenzo[b]thiophene-3-carboxylic acid | B |
| 2-(4-Fluoro-2-methylbenzenesulphonylamino)-4,5,6,7-tetrahydrobenzo[b]thiophene-3-carboxylic acid | B |
| 2-Benzenesulphonylamino-5-(furan-3-yl)-4-methylthiophene-3-carboxylic acid | B |
| 2-(2-Ethylbenzenesulphonylamino)-4,5,6,7-tetrahydrobenzo[b]thiophene-3-carboxylic acid | A |
| 2-[2-((Z)-3-Diethylaminoprop-1-enyl)benzenesulphonylamino]-4,5,6,7-tetrahydrobenzo[b]thiophene-3-carboxylic acid | B |

-continued

| Compound name | Activity |
|---|---|
| 2-Benzenesulphonylamino-5,6-dihydro-4H-cyclopenta[b]thiophene-3-carboxylic acid | B |
| 2-(4-Chlorobenzenesulphonylamino)-4,5,6,7-tetrahydrobenzo[b]thiophene-3-carboxylic acid | B |
| 2-(3-Chlorobenzenesulphonylamino)-4,5,6,7-tetrahydrobenzo[[b]thiophene-3-carboxylic acid | B |

Incorporation By Reference

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound represented by Formula I:

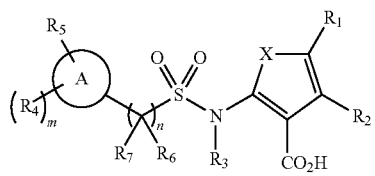

and pharmaceutically acceptable salts, stereoisomers, esters and prodrugs thereof, wherein X is S;

$R_1$ and $R_2$ are joined together with the ring they are attached to form a moiety selected from:

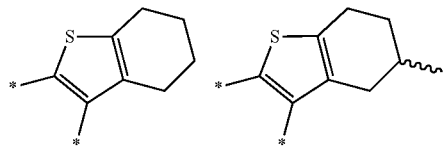

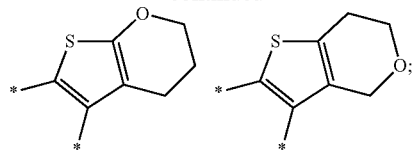

$R_3$ is selected from the group consisting of hydrogen or $C_{1-6}$alkyl, wherein $C_{1-6}$alkyl may be optionally substituted by one or more substituents selected from the group consisting of halogen, hydroxyl, $C_{1-6}$alkoxy, $C_{3-6}$cycloalkyl, or $R^cR^dN$—;

wherein:

(i) when $R_1$ and $R_2$ are joined together with the ring they are attached to form

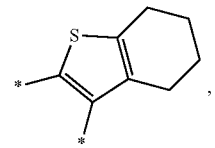

$R_4$ is selected from the group consisting of fluoro; cyano; $C_{1-6}$alkyl substituted by one or more halogens; unsubstituted $C_{2-6}$alkyl selected from the group consisting of ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl; $C_{2-6}$alkenyl; $C_{2-6}$alkynyl; $C_{3-6}$cycloalkyl; and $C_{1-6}$alkoxy, wherein $C_{1-6}$alkoxy, $C_2$-6alkenyl, $C_{3-6}$cycloalkyl and $C_{2-6}$alkynyl may be optionally substituted by one or more halogens;

m is 1, 2, or 3; and $R_5$ is selected from the group consisting of hydrogen, $C_{1-6}$alkyl substituted by one or more substituents selected from halogen, hydroxyl, $C_{1-4}$alkoxy, $C_{1-6}$alkyl, $C_{3-6}$cycloalkyl, cyano, phenyl, heteroaryl and heterocyclyl; unsubstituted $C_{2-6}$alkyl selected from the group consisting of ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl; $C_{1-6}$alkoxy; $C_{2-6}$alkenyl; $C_{2-6}$alkynyl; $C_{3-6}$cycloalkyl; $C_{3-6}$cycloalkyl$C_{1-6}$alkyl—; $C_{1-6}$alkyl-S(O)$_w$- wherein w is 0, 1 or 2; $C_{1-6}$alkyl-N($R^c$)-carbonyl; $C_{1-6}$alkyl-carbonyl-N($R^c$)—; $C_{1-6}$alkyl-N($R^c$)-carbonyl-N($R^c$)—; and $C_{1-6}$ alkyl-N($R^c$)—; wherein $C_{1-6}$alkoxy, $C_{2-6}$alkenyl, $C_{3-6}$cycloalkyl and $C_{2-6}$alkynyl may be optionally substituted by one or more substituents selected from halogen, hydroxyl, $C_{1-4}$alkoxy, $C_{1-6}$alkyl, $C_{3-6}$cycloalkyl, cyano, phenyl, heteroaryl and heterocyclyl; wherein phenyl or heteroaryl is optionally substituted with one or more substituents selected from $R^a$; wherein said heteroaryl is a 5-6 membered ring having one, two, or three heteroatoms selected from O, S, or N, wherein said heterocyclyl is a 4-7 membered ring optionally substituted by one or more substituents selected from $R^b$ and wherein if said heterocyclyl contains a —NH moiety that nitrogen may be optionally substituted by one or more groups $R^f$;

or (ii) when $R_1$ and $R_2$ are joined together with the ring they are attached to form

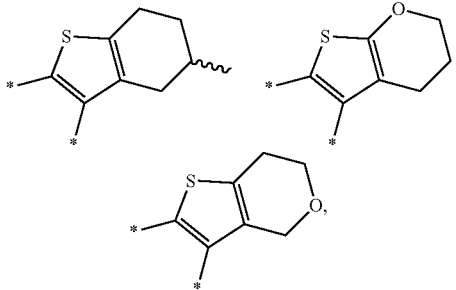

$R_4$ is selected from the group consisting of halogen, cyano, $C_{1-6}$alkyl, $C_{2-6}$alkenyl, $C_{2-6}$alkynyl, $C_{3-6}$cycloalkyl, and $C_{1-6}$alkoxy, wherein $C_{1-6}$alkyl, $C_{1-6}$alkoxy, $C_{2-6}$alkenyl, $C_{3-6}$cycloalkyl and $C_{2-6}$alkynyl may be optionally substituted by one or more halogens;

m is 0, 1, 2, or 3; and $R_5$ is selected from the group consisting of hydrogen, $C_{1-6}$alkyl, $C_{2-6}$alkenyl, $C_{2-6}$alkynyl, $C_{3-6}$cycloalkyl, $C_{1-6}$alkoxy, $C_{3-6}$cycloalkyl$C_{1-6}$alkyl-, $C_{1-6}$alkyl-S(O)$_w$— wherein w is 0, 1 or 2, $C_{1-6}$ alkyl-N($R^c$)-carbonyl, $C_{1-6}$alkyl-carbonyl-N($R^c$)—, $C_{1-6}$alkyl-N($R^c$)-carbonyl-N($R^c$)—, and $C_{1-6}$alkyl-N($R^c$)—, wherein $C_{1-6}$alkyl, $C_{1-6}$alkoxy, $C_{2-6}$alkenyl, $C_{3-6}$cycloalkyl and $C_{2-6}$alkynyl may be optionally substituted by one or more substituents selected from halogen, hydroxyl, $C_{1-4}$alkoxy, $C_{1-6}$alkyl, $C_{3-6}$cycloalkyl, cyano, phenyl, heteroaryl and heterocyclyl; wherein phenyl or heteroaryl is optionally substituted with one or more substituents selected from $R^a$; wherein said heteroaryl is a 5-6 membered ring having one, two, or three heteroatoms selected from O, S, or N, and wherein said heterocyclyl is a 4-7 membered ring optionally substituted by one or more substituents selected from $R^b$ and wherein if said heterocyclyl contains a —NH moiety that nitrogen may be optionally substituted by one or more groups $R^f$;

$R_6$ and $R_7$ are each independently selected from the group consisting of hydrogen, halogen, $C_{1-6}$alkyl, $C_{2-6}$alkenyl, $C_{3-6}$alkynyl, and $C_{3-6}$cycloalkyl; or $R_6$ and $R_7$ taken together with the carbon to which they are attached form a cyclopropyl ring or 4-6 membered ring which may optionally have one atom or group selected from N($R^c$), O or S(O)$_p$; wherein said ring may be optionally substituted by one or more $C_{1-6}$alkyl substituents; and wherein $C_{1-6}$alkyl, $C_{2-6}$alkenyl, $C_{3-6}$alkynyl, and $C_{3-6}$cycloalkyl may be optionally substituted by one or more substituents selected from the group consisting of halogen, hydroxyl, $R^cR^dN$—, $C_{1-4}$alkoxy, $C_{3-6}$cycloalkyl, and $C_{1-6}$alkyl;

A is phenyl;

n is 0, 1, or 2;

$R^a$ is independently selected, for each occurrence, from the group consisting of halogen, hydroxyl, cyano, $C_{1-6}$alkyl, $C_{3-6}$cycloalkyl, $C_{1-6}$alkoxy, $R^cR^dN$—, $R^cR^dN$-carbonyl, $C_{1-6}$alkyl, $R^cR^dN$-carbonyl-N($R^c$)—; $R^cR^dN$—SO$_2$—, $R^cR^dN$—SO$_2$—N($R^c$)—; and $C_{1-6}$alkyl-carbonyl-N($R^c$)—, wherein $C_{1-6}$alkyl, $C_{2-6}$alkoxyl, and $C_{3-6}$cycloalkyl may be optionally substituted by one or more substituents selected from halogen, hydroxyl, $R^cR^dN$—, $C_{1-4}$alkoxy, $C_{3-6}$cycloalkyl, and $C_{1-6}$alkyl;

$R^b$ is independently selected, for each occurrence, from the group consisting of halogen, hydroxyl, cyano, oxo, $C_{1-6}$alkyl, or $C_{1-6}$alkoxy,, wherein $C_{1-6}$alkyl, and $C_{1-6}$alkoxy, may be optionally substituted by one or more substituents selected from halogen, hydroxyl, $C_{1-4}$alkoxy, $C_{3-6}$cycloalkyl, and $C_{1-6}$alkyl;

$R^c$ and $R^d$ independently selected, for each occurrence, from the group consisting of hydrogen or $C_{1-6}$alkyl optionally substituted by one or more halogens; or $R^c$ and $R^d$, if they occur together, may form a 4-7 membered heterocyclyl together with the nitrogen to which they are attached, which may be optionally substituted by one or more substituents selected from $R^b$;

and $R^f$ is selected from the group consisting of $C_{1-6}$alkyl, $C_{1-6}$alkylcarbonyl, or $C_{1-6}$alkylsuphonyl, wherein $C_{1-6}$alkyl, may be optionally substituted by one or more halogens.

2. The compound of claim 1, wherein $R_1$ and $R_2$ are joined together with the ring they are attached to form

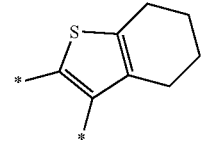

3. The compound of claim 1, wherein $R_4$ is fluoro.

4. The compound of claim 1, wherein $R_3$ is H.

5. The compound of claim 1, wherein $R_5$ is selected from the group consisting of H, $C_{1-6}$alkoxy, $C_{1-6}$alkyl, $C_{2-6}$alkenyl, $C_{2-6}$alkynyl, $C_{3-6}$cycloalkyl, $C_{3-6}$cycloalkyl$C_{1-6}$alkyl-, $C_{1-6}$alkyl-S(O)$_w$— wherein w is 0, 1 or 2, $C_{1-6}$ alkyl-N($R^c$)-carbonyl, $C_{1-6}$alkyl-carbonyl-N($R^c$)—, $C_{1-6}$alkyl-N($R^c$)-carbonyl-N($R^c$)—, and $C_{1-6}$ alkyl- N($R^c$).

6. The compound of claim 1, wherein n is 0.

7. A compound selected from the group consisting of 2-(4-fluorobenzenesulphonylamino)-4,5,6,7-tetrahydrobenzo[b]thiophene-3-carboxylic acid, 2-benzenesulphonylaminobenzo(b)thiophene-3-carboxylic acid, 2-benzenesulphonylamino-5-ethyl-4-methylthiophene-3-carboxylic acid, 2-benzenesulphonylamino-4,7-dihydro-5H-thieno[2,3-c]pyran-3-carboxylic acid, 2-benzenesulphonylamino-4-methyl-5-phenylthiophene-3-carboxylic acid, 2-benzylsulphonylamino-4,5,6,7-tetrahydrobenzo[b]thiophene-3-carboxylic acid, 2-benzenesulphonylamino-5,5-dimethyl-4,5,6,7-tetrahydrobenzo[b]thiophene-3-carboxylic acid, 2-benzenesulphonylamino-6,7-dihydro-4H-thieno[3,2-c]pyran-3-carboxylic acid, 2-benzenesulphonylamino-3,4-dihydro-2H-thieno[2,3-b]pyran-5-carboxylic acid, 2-benzenensulphonylamino-5-methyl-4,5,6,7-tetrahydrobenzo[b]thiophene-3-carboxylic acid, 2-benzenesulphonylamino-6-methyl-4,5,6,7-tetrahydrobenzo [b]thiophene-3 -carboxylic acid, 2-benzenesulphonylamino-6,6-dimethyl-4,5,6,7-tetrahydrobenzo[b]thiophene-3-carboxylic acid, 2-benzenesulphonylamino-l-methyl-4,5,6,7-tetrahydro-1H-indole-3-carboxylic acid, 2-benzenesulphonylamino-5-(tetrahydropyran-4-yl)thiophene-3-carboxylic acid, 2-benzenesulphonylamino-5-ethyl-4-isopropylthiophene-3-carboxylic acid, 2-(2-trifluoromethylbenzenesulphonylamino)-4,5,6,7-tetrahydrobenzo[b]thiophene-3-carboxylic acid, 2-(2-fluorobenzenesulphonylamino)-4,5,6,7-tetrahydrobenzo[b]thiophene-3-carboxylic acid, 2-(cyclohexanesulphonylamino)-4,5,6,7-tetrahydrobenzo[b]thiophene-3-carboxylic acid, 2-(2-methoxybenzenesulphonylamino)-4,5,6,7-tetrahydrobenzo[b]thiophene-3-carboxylic acid, 2-(3-methoxybenzenensulphonylamino)-4,5,6,7-tetrahydrobenzo[b]thiophene-3-carboxylic acid, 2-(4-fluoro-2-methylbenzenesulphonylamino)-4,5,6,7-tetrahydrobenzo[b]thiophene-3-carboxylic acid, benzenesulphonylamino-5-(furan-3-yl)-4-methylthiophene-3-carboxylic acid, and 2-(2-ethylbenzenesulphonylamino)-4,5,6,7-tetrahydrobenzo[b]thiophene-3-carboxylic acid, or a pharmaceutically acceptable salt thereof.

8. A pharmaceutical composition comprising a compound of claim 1, and a pharmaceutically acceptable carrier.

9. The composition of claim 8, wherein the composition is formulated as a unit dose.

10. The composition of claim 9, wherein the composition is formulated for oral administration.

11. The composition of claim 8, wherein the composition is formulated for intravenous or subcutaneous administration.

12. The compound of claim 2, wherein $R_4$ is selected from the group consisting of fluoro, unsubstituted $C_{2-6}$allcyl, $C_{1-6}$alkyl substituted by one or more halogens, and $C_{1-6}$alkoxy.

13. The compound of claim 1, wherein $R_5$ is H.

14. The compound of claim 1, wherein m is 0.

15. A method of treating and/or controlling obesity, comprising administering to a patient in need thereof an effective amount of a compound of claim 1.

16. A method of inducing weight loss in a patient in need thereof, comprising administering to said patient an effective amount of a compound of claim 1.

17. The method of claim 15, wherein the patient is a human.

18. The method of claim 15, wherein the patient has a body mass index greater than or equal to about 30 kg/m$^2$ before the administration.

19. The method of claim 15, wherein the compound is administered orally.

* * * * *